US011684299B2

(12) United States Patent
Levy

(10) Patent No.: US 11,684,299 B2
(45) Date of Patent: Jun. 27, 2023

(54) METHOD AND SYSTEM FOR REMOTELY MONITORING THE PSYCHOLOGICAL STATE OF AN APPLICATION USER USING MACHINE LEARNING-BASED MODELS

(71) Applicant: Mahana Therapeutics, Inc., San Francisco, CA (US)

(72) Inventor: Simon Levy, San Francisco, CA (US)

(73) Assignee: Mahana Therapeutics, Inc., San Francisco, CA (US)

( * ) Notice: Subject to any disclaimer, the term of this patent is extended or adjusted under 35 U.S.C. 154(b) by 644 days.

(21) Appl. No.: 16/717,295

(22) Filed: Dec. 17, 2019

(65) Prior Publication Data

US 2021/0177324 A1    Jun. 17, 2021

(51) Int. Cl.
| | |
|---|---|
| *A61B 5/16* | (2006.01) |
| *A61B 5/00* | (2006.01) |
| *G06N 5/04* | (2023.01) |
| *G09B 7/00* | (2006.01) |
| *G06N 20/00* | (2019.01) |

(52) U.S. Cl.
CPC .............. *A61B 5/165* (2013.01); *A61B 5/162* (2013.01); *A61B 5/7267* (2013.01); *A61B 5/7275* (2013.01); *A61B 5/747* (2013.01); *A61B 5/7475* (2013.01); *G06N 5/04* (2013.01); *G06N 20/00* (2019.01); *G09B 7/00* (2013.01)

(58) Field of Classification Search
CPC .................................. G09B 7/00; G06N 20/00
See application file for complete search history.

(56) References Cited

U.S. PATENT DOCUMENTS

| | | | |
|---|---|---|---|
| 9,467,789 | B1 | 10/2016 | Zhao et al. |
| 9,536,052 | B2 | 1/2017 | Amarasingham et al. |
| 9,642,573 | B2 | 5/2017 | Zhao et al. |
| 10,595,159 | B1 | 3/2020 | Nelson et al. |
| 11,045,126 | B2 | 6/2021 | Matic et al. |
| 11,164,596 | B2 | 11/2021 | Jain et al. |

(Continued)

FOREIGN PATENT DOCUMENTS

| | | |
|---|---|---|
| EP | 3711666 | 9/2020 |
| JP | 4781710 | 7/2011 |

(Continued)

OTHER PUBLICATIONS

Dang, et al. "Role of digital therapeutics and the changing future of healthcare," Journal of Family Medicine and Primary Care, May 31, 2020, vol. 9, issue 5, pp. 2207-2213.

(Continued)

*Primary Examiner* — Peter R Egloff
(74) *Attorney, Agent, or Firm* — Hawley Troxell Ennis & Hawley LLP; Rivkah Young

(57) ABSTRACT

An application user is granted access to one or more applications that provide the user with information and assistance. Through the one or more applications, the user is provided with interactive content, and data related to aspects of the user's interaction with the provided content is collected. The collected interaction data is analyzed to remotely identify and monitor changes or anomalies in the psychological state of the user using machine learning-based models. Upon identification of changes or anomalies in the user's psychological state, one or more actions are taken to assist the user.

10 Claims, 6 Drawing Sheets

(56) References Cited

U.S. PATENT DOCUMENTS

| | | |
|---|---|---|
| 2006/0136173 A1 | 6/2006 | Case et al. |
| 2010/0169409 A1 | 7/2010 | Fallon et al. |
| 2011/0077971 A1 | 3/2011 | Surwit et al. |
| 2011/0172059 A1 | 7/2011 | Watterson et al. |
| 2012/0035021 A1 | 2/2012 | Saalasti et al. |
| 2012/0083705 A1 | 4/2012 | Yuen et al. |
| 2012/0150074 A1 | 6/2012 | Yanev et al. |
| 2012/0226472 A1 | 9/2012 | Yuen et al. |
| 2014/0247989 A1 | 9/2014 | Deaver |
| 2014/0313030 A1 | 10/2014 | Ten Kate et al. |
| 2014/0377727 A1 | 12/2014 | Yom-Tov et al. |
| 2015/0037315 A1 | 2/2015 | Matharu et al. |
| 2015/0314102 A1 | 11/2015 | Rosenberg et al. |
| 2016/0001096 A1 | 1/2016 | Mishelevich et al. |
| 2016/0063874 A1 | 3/2016 | Czerwinski |
| 2016/0120732 A1 | 5/2016 | Hathorn |
| 2016/0140320 A1 | 5/2016 | Moturu et al. |
| 2016/0317781 A1 | 11/2016 | Proud |
| 2017/0035346 A1 | 2/2017 | Apte et al. |
| 2017/0109437 A1 | 4/2017 | Kudo et al. |
| 2017/0281060 A1 | 10/2017 | Wedekind et al. |
| 2017/0329933 A1 | 11/2017 | Brust et al. |
| 2017/0340270 A1 | 11/2017 | Ganesh |
| 2018/0052962 A1 | 2/2018 | Van der Koijk et al. |
| 2018/0060494 A1 | 3/2018 | Dias et al. |
| 2018/0089385 A1 | 3/2018 | Gupta et al. |
| 2018/0107793 A1 | 4/2018 | Ni et al. |
| 2018/0122510 A1 | 5/2018 | Apte et al. |
| 2018/0285528 A1 | 10/2018 | Healey et al. |
| 2018/0330824 A1 | 11/2018 | Athey et al. |
| 2018/0357562 A1* | 12/2018 | Hofman ................ G06N 5/022 |
| 2019/0019581 A1 | 1/2019 | Vaughan et al. |
| 2019/0043610 A1 | 2/2019 | Vaughn |
| 2019/0050774 A1 | 2/2019 | Divine et al. |
| 2019/0066834 A1 | 2/2019 | Van Tuyl et al. |
| 2019/0088366 A1 | 3/2019 | Vaughn et al. |
| 2019/0109830 A1 | 4/2019 | McFarland et al. |
| 2019/0159716 A1 | 5/2019 | Alailima et al. |
| 2019/0216392 A1 | 7/2019 | Bower et al. |
| 2019/0236923 A1 | 8/2019 | Devdas et al. |
| 2019/0298917 A1 | 10/2019 | Malave et al. |
| 2019/0313934 A1 | 10/2019 | Lee et al. |
| 2019/0335006 A1* | 10/2019 | George ................ G06N 3/0454 |
| 2019/0388733 A1 | 12/2019 | Ackland |
| 2020/0082735 A1* | 3/2020 | Nel ..................... G09B 19/00 |
| 2020/0082927 A1 | 3/2020 | Hernandez |
| 2020/0245009 A1 | 7/2020 | Saini et al. |
| 2020/0411185 A1 | 12/2020 | Oser et al. |
| 2021/0145338 A1 | 5/2021 | Borthakur |
| 2021/0183481 A1 | 6/2021 | Levy |
| 2021/0183482 A1 | 6/2021 | Levy |
| 2021/0375423 A1 | 12/2021 | Levy |
| 2021/0375424 A1 | 12/2021 | Levy |
| 2021/0375465 A1 | 12/2021 | Levy |
| 2022/0028528 A1 | 1/2022 | Paull et al. |
| 2022/0028529 A1 | 1/2022 | Paull et al. |
| 2022/0028541 A1 | 1/2022 | Paull et al. |
| 2022/0130510 A1 | 4/2022 | Levy |
| 2022/0130513 A1 | 4/2022 | Levy |
| 2022/0130514 A1 | 4/2022 | Levy |
| 2022/0130515 A1 | 4/2022 | Levy |
| 2022/0130516 A1 | 4/2022 | Levy |
| 2022/0130539 A1 | 4/2022 | Levy |

FOREIGN PATENT DOCUMENTS

| | | |
|---|---|---|
| JP | 6684820 | 1/2020 |
| KR | 10-2018-0006692 | 1/2018 |
| KR | 10-2019-0009946 | 1/2019 |
| WO | WO 2007/13 0491 | 11/2007 |
| WO | WO 2007/130491 | 11/2007 |
| WO | WO 2010/009278 | 1/2010 |
| WO | WO 2011/105914 | 9/2011 |
| WO | WO 2017/106770 | 6/2017 |
| WO | WO 2017/214630 | 12/2017 |
| WO | WO 2018/071886 | 4/2018 |
| WO | WO 2018/077844 | 5/2018 |
| WO | WO 2019/040918 | 2/2019 |
| WO | WO 2019/123463 | 6/2019 |
| WO | WO 2021/032327 | 2/2021 |

OTHER PUBLICATIONS

Brown, A. M., "An App for Every Psychological Problem: Vision for the Future" (Order No. 10032397). Available from ProQuest Dissertations and Theses Professional. (1773418320). Retrieved from https://dialog.proquest.com/professional/docview/1773418320?accountid=131444 (Year: 2016).

Brown, A. M., "An App for Every Psychological Problem: Vision for the Future" (Order No. 10032397). Available from ProQuest Dissertations and Theses Professional. (1773418320). Retrieved from https://dialog.proquest.eom/professional/docview/1773418320?accountid=131444 (Year: 2016).

Burkhouse et al., Neural Reactivity to Reward as a Predictor of Cognitive Behavioral Therapy Response in Anxiety and Depression, Depress Anxiety, 33(4), 281-288, Apr. 2016 (Year: 2016).

* cited by examiner

METHOD AND SYSTEM FOR REMOTELY MONITORING THE PSYCHOLOGICAL STATE OF AN APPLICATION USER USING MACHINE LEARNING-BASED MODELS

RELATED APPLICATIONS

This application is related to U.S. patent application Ser. No. 16/717,287, naming Simon Levy as inventor, filed concurrently with the present application on Dec. 17, 2019, entitled "METHOD AND SYSTEM FOR REMOTELY MONITORING THE PSYCHOLOGICAL STATE OF AN APPLICATION USER BASED ON AVERAGE USER INTERACTION DATA," which is hereby incorporated by reference in its entirety as if it were fully set forth herein. This application is also related to U.S. patent application Ser. No. 16/717,291, naming Simon Levy as inventor, filed concurrently with the present application on Dec. 17, 2019, entitled "METHOD AND SYSTEM FOR REMOTELY MONITORING THE PSYCHOLOGICAL STATE OF AN APPLICATION USER BASED ON HISTORICAL USER INTERACTION DATA," which is hereby incorporated by reference in its entirety as if it were fully set forth herein.

BACKGROUND

In recent years, digital applications have come to play an increasingly large role in the daily lives of billions of people all over the world. Currently, a vast number of applications are readily available to users over a wide variety of technologies. These applications range greatly in type and purpose, providing users with information and services such as productivity tools, educational materials, and entertainment options. As technology advances, these applications are becoming more and more sophisticated in terms of the content and experiences they are able to provide to users. For example, in addition to providing users with information and other types of static content, most modern applications are also able to provide users with a variety of interactive features, thereby allowing a user to select specific and/or customized content based on user input, user interactions, and user behavior. In this way, the benefits an application provides to a user can be customized to meet the needs or desires of specific individuals.

Due to the increased use of these digital applications in the daily lives of users, many such applications are now being used to supplement or replace traditional human to human, i.e., in person, interactions. Further, it has become increasingly clear that this trend will continue to grow in the years to come. However, while these types of interactive applications can provide many beneficial features to users, currently, these applications still present a variety of limitations that need to be addressed in order for this interactive technology to achieve its fullest potential.

As a specific example, every day, millions of people are diagnosed with a wide variety of medical conditions, ranging greatly in type and severity. A patient who has been diagnosed with a medical condition often experiences many hardships as a result of their diagnosis. In addition to physical effects, such as pain, discomfort, or loss of mobility that may accompany the diagnosis, the hardships faced by patients often further include financial difficulties resulting from lost work, medical bills and the cost of treatments. Further still, a patient's diagnosis often negatively impacts their social interactions and overall emotional well-being. The result is that many patients experience significant psychological distress as a result of their diagnosis, and often do not receive adequate support or treatment to alleviate this distress.

Often, when a patient is diagnosed with one or more medical conditions, the patient may be referred to additional health professionals for further care and treatment. For example, a patient may be referred to a psychologist, psychiatrist, counselor, or other mental health professional. A patient may also be directed to one or more support groups to assist with any psychological distress that the patient may be experiencing. While these traditional face-to-face options may be greatly beneficial to a patient, often times they do not provide enough psychological support. For example, when a patient is alone, at home, or not otherwise engaged directly with their mental health professional or support group, they may experience a significant degree of one or more negative emotional states, such as fear, anxiety, panic, and depression. Additionally, left unidentified and untreated, these negative emotional states often exacerbate the physical symptoms associated with a patient's diagnosis, which in turn can lead to greater psychological distress.

Further, while some patients may recognize that they are, for example, anxious or distressed, and may actively seek out additional help, many patients may experience these mental states without fully recognizing them, and thus might not realize that they are in need of additional help. Further still, many patients may feel embarrassed or ashamed about their medical condition, which may discourage them from actively reaching out for the help that they need. Consequently, the shortcomings associated with traditional psychological support and treatment mechanisms can have significant and serious effects on a patient's overall health, safety, and well-being.

Because current mechanisms for enabling mental health professionals to monitor the psychological state of patients outside of a medical office or support group setting are limited, the shortcomings associated with traditional psychological support and treatment options presents a technical problem, which requires a technical solution. As digital applications begin to replace human interactions, this problem becomes even more pronounced. This is because people are increasingly relying on applications to provide them with support and assistance in a wide variety of aspects of their daily lives, and the failure of traditional solutions to address these issues has the potential to lead to significant consequences for a large number of people.

What is needed, therefore, is a method and system to more accurately and remotely identify and monitor changes or anomalies in a patient's psychological state in order to ensure that they receive adequate care, support, and treatment.

SUMMARY

Embodiments of the present disclosure provide an effective and efficient technical solution to the technical problem of accurately and remotely identifying and monitoring changes or anomalies in the psychological state of a current user of one or more applications by monitoring the current user's interaction with the various materials presented through the application interfaces of the one or more applications to obtain current user interaction data. In one embodiment, the current user interaction data is then compared to average user interaction data associated with average users to determine the current user's mental state and/or detect any anomalies in the current user's mental state. In one embodiment, the current user's interaction data is compared with historical user interaction data associated with the current user to determine the current user's mental state and/or detect any anomalies in the current user's mental state. In one embodiment, the current user's interaction data is processed using one or more machine learning based mental state prediction models to determine the current user's mental state and/or detect any anomalies in the current user's mental state.

Some embodiments of the present disclosure provide an effective and efficient technical solution to the technical problem of accurately and remotely identifying and monitoring changes or anomalies in the psychological state of patients who have been diagnosed with one or more medical conditions. In the disclosed embodiments, a patient diagnosed with one or more medical conditions is prescribed access to a digital therapeutics application, which is designed to provide guided care to the patient in a variety of ways.

In one embodiment, once a patient has been prescribed access to the digital therapeutics application, the patient is free to access the application and utilize the tools provided by the application. Once the patient accesses the application, the patient becomes a user of the application, and is provided with digital content through a user interface of the application. The content provided to the user may include information relating to one or more of the user's medical conditions, as well as information relating to the user's current and potential medications and/or treatments. The content provided to the user may further include interactive content, such as questions or exercises related to the content, which are designed to encourage the user to interact with a variety of multi-media materials through the application interface.

In one embodiment, the user's interaction with the various materials presented through the application interface is monitored to obtain user interaction data. User interaction data may include data such as the user's speed of interaction with the materials presented, as well as the user's comprehension of the materials presented. In various embodiments, the user's speed of interaction with the materials presented can be determined in a variety of ways such as, but not limited to, monitoring the rate at which the user scrolls through text data, the rate at which the user clicks buttons that advance the user through the materials, or the rate at which the user types textual strings in response to questions or exercises provided by the application. In various embodiments, other user data such as, but not limited to, user audio data, user video data, and/or user biometric data such as eye scan rate data, can be used to monitor the user's speed of interaction. The user's comprehension of the materials presented can also be determined in a variety of ways, such as, but not limited to, intermittently presenting the user with questions about the content while the user is engaged with the application.

In some embodiments, the digital therapeutics application obtains interaction data from a plurality of application users and processes this data to compute an average interaction speed and an average comprehension level, based on the interaction data associated with the plurality of users. In some embodiment, this information may be obtained from third parties in a more general form, such as average reading speed for a given demographic sector of the population. A particular user may then be presented with interactive content, and the user's interaction speed and comprehension level may be monitored and compared to the averages to determine whether the particular user's interaction speed and/or comprehension level are within a predefined threshold of the computed averages. Upon a determination that the user's interaction speed and/or comprehension level are outside of the predefined threshold, a prediction may be made, based on this determination, as to the likely mental state of the application user, and additional action may be taken, as will be discussed in further detail below.

In some embodiments, once a user has been prescribed access to the digital therapeutics application, a user profile is generated for that particular user. As the user interacts with the application content, the user's interaction speed and comprehension level for each interaction session are monitored and the resulting interaction data may be stored in a database associated with the user's profile. The user's interaction data is then analyzed to determine the user's baseline interaction speed and comprehension level. The user's baseline may be periodically or continually updated over time. Each time the user accesses and interacts with the application, the resulting interaction data for the current interaction session may be compared to the user's baseline to determine whether the user's interaction speed and/or comprehension level are within a predefined threshold of the user's baseline. Upon a determination that the user's interaction speed and/or comprehension level are outside of the predefined threshold, a prediction may be made, based on this determination, as to the likely mental state of the application user, and additional action may be taken, as will be discussed in further detail below.

In some embodiments, multiple users are provided with information and interactive content through a user interface of the digital therapeutics application. Each user's interactions are monitored to collect user interaction data, such as interaction speed and comprehension level. Additionally, mental state data is collected for each of the users, and the mental state data is correlated with the user interaction data. The correlated mental state and user interaction data is then utilized as training data to generate one or more trained machine learning based mental state prediction models.

Once one or more machine learning models have been generated, a current user may be provided with information and interactive content through the user interface of the application. The current user's interactions are monitored to collect user interaction data, which is then provided to the one or more trained machine learning based mental state prediction models, resulting in the generation of user mental state prediction data for the current user.

In various embodiments, upon either identifying the likely mental state of a user, or identifying a change or anomaly in the mental state of a user, additional actions may be taken by the digital therapeutics application to assist the user, depending on the user's particular mental state or known medical conditions, and also depending upon a determination of the severity of the change or anomaly. For example, if a determination is made that a user who is normally calm is currently in a mildly anxious mental state, minor actions may be taken, such as adjusting the content and/or presentation of the information that is being provided to the user through the user interface. On the other hand, if a user who is normally mildly anxious is currently in a severely anxious, fearful, or depressed state, more extreme actions may be taken, such as notifying one or more medical professionals associated with the user through a notification system of the application, or some other form of personal intervention from one or more medical professionals associated with the user.

As a result of these and other disclosed features, which are discussed in more detail below, the disclosed embodiments provide an effective and efficient technical solution to the technical problem of remotely identifying and monitoring changes or anomalies in the psychological state of application users, including users who have been diagnosed with one or more medical conditions.

Figure 1:
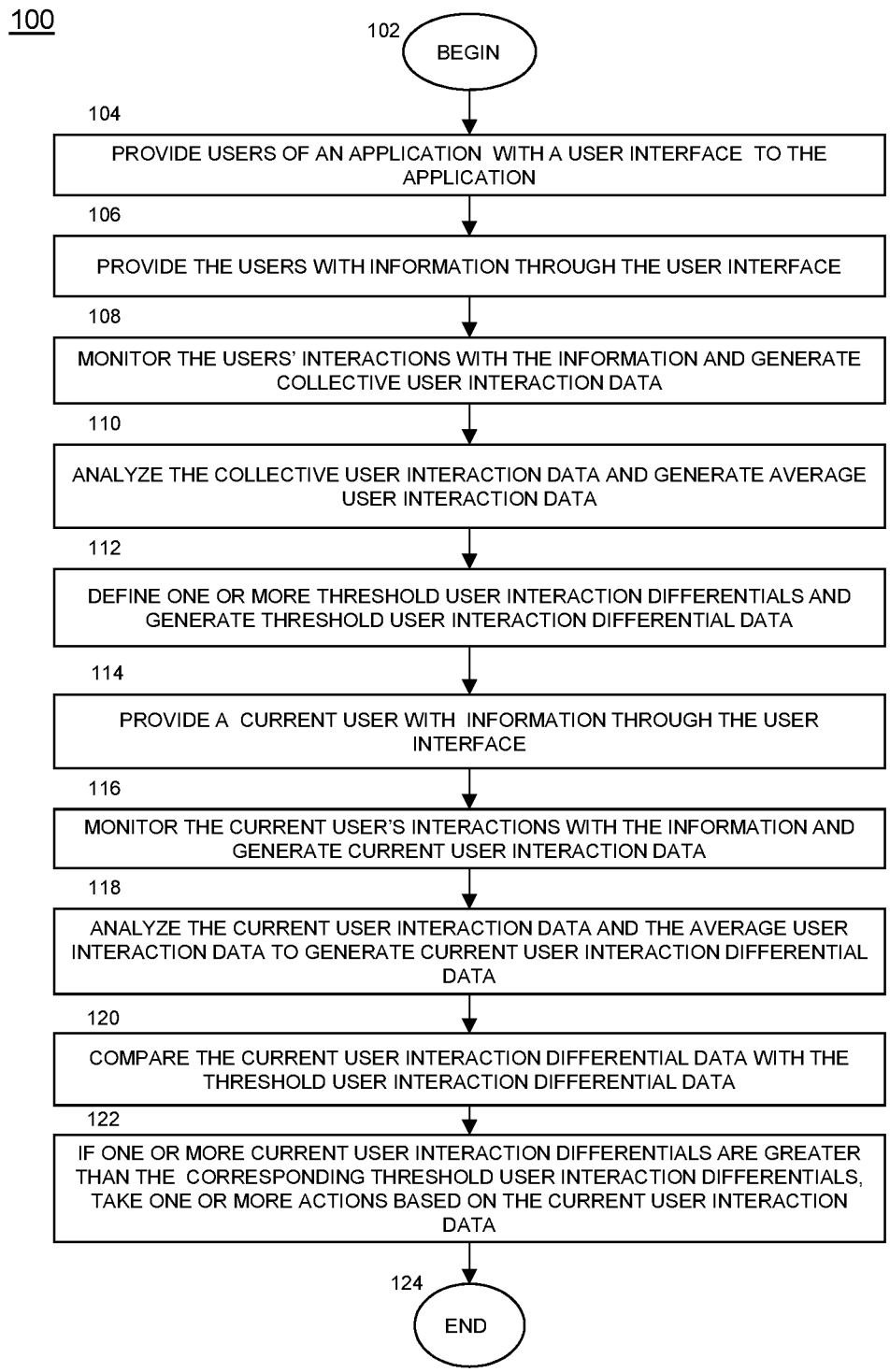
FIG. 1 is a flow chart of a process for remotely identifying and monitoring anomalies in the psychological state of application users based on analysis of average user interaction data and current user interaction data in accordance with a first embodiment.

Common reference numerals are used throughout the figures and the detailed description to indicate like elements. One skilled in the art will readily recognize that the above figures are merely illustrative examples and that other architectures, modes of operation, orders of operation, and elements/functions can be provided and implemented without departing from the characteristics and features of the invention, as set forth in the claims.

DETAILED DESCRIPTION

Embodiments will now be discussed with reference to the accompanying figures, which depict one or more exemplary embodiments. Embodiments may be implemented in many different forms and should not be construed as limited to the embodiments set forth herein, shown in the figures, or described below. Rather, these exemplary embodiments are provided to allow a complete disclosure that conveys the principles of the invention, as set forth in the claims, to those of skill in the art.

Embodiments of the present disclosure provide an effective and efficient technical solution to the technical problem of remotely identifying and monitoring changes or anomalies in the psychological state of application users. In the disclosed embodiments, a user is granted access to one or more applications designed to provide the user with information and assistance in a variety of ways. Through the one or more applications, the user may be provided with interactive content, which allows for the collection of data related to aspects of the user's interaction with the provided content. The collected interaction data is then analyzed to identify and monitor changes or anomalies in the psychological state of the user. Upon identification of changes or anomalies in the user's psychological state, one or more actions are taken to assist the user.

FIG. 1 is a flow chart of a process 100 for remotely identifying and monitoring anomalies in the psychological state of application users based on analysis of average user interaction data and current user interaction data in accordance with a first embodiment.

Process 100 begins at BEGIN 102 and process flow proceeds to 104. At 104, one or more users of an application are provided with a user interface, which allows the one or more users to receive output from the application, as well as to provide input to the application.

In various embodiments, the application may be any type of application that is capable of providing content/information to a user through a user interface, including, but not limited to, a desktop computing system application, a mobile computing system application, a virtual reality computing system application, an application provided by an Internet of Things (IoT) device, or any combination thereof. In various embodiments, the user interface may include any combination of a graphical user interface, an audio-based user interface, a touch-based user interface, or any other type of user interface currently known to those of skill in the art, or any other type of user interface that may be developed after the time of filing.

In one embodiment, the application provided to the one or more users is a digital therapeutics application, which is designed to assist patients who have been diagnosed with one or more medical conditions. As a specific illustrative example, upon diagnosing a patient with one or more medical conditions, a medical care professional may prescribe the patient access to the digital therapeutics application. The digital therapeutics application may be accessed by the patient through any type of computing system that is capable of providing a user interface to a user, as discussed above. Upon accessing the digital therapeutics application, the patient then becomes a user of the application, and is provided with a user interface, which enables the user to interact with the digital therapeutics application.

In one embodiment, once one or more users of an application are provided with a user interface at 104, process flow proceeds to 106. At 106, the one or more users are provided with information through the user interface.

In various embodiments, the information provided to the one or more users through the user interface includes, but is not limited to, textual information, audio information, graphical information, image information, video information, and/or any combination thereof. In one embodiment, the information is provided to the one or more users in such a way that allows the one or more users to interact with the information provided. For example, a user may be presented with information on the screen of an electronic device, along with a variety of graphical user elements, which allow the user to scroll through the information, click on buttons associated with the information, and/or enter textual strings in response to the information. When the information is presented to a user on a device that includes a touch screen, the interaction may include touch-based interactions and/or gesture recognition. In addition to textual inputs and touch or click-based inputs, in various embodiments, the user may be able to interact with the information through more advanced input mechanisms such as through audio input, video input, accelerometer input, voice recognition, facial recognition or through a variety of physiological sensors. Examples of physiological sensors may include, but are not limited to, heart rate monitors, blood pressure monitors, eye tracking monitors, or muscle activity monitors.

As one specific illustrative example, in one embodiment, once one or more users of a digital therapeutics application are provided with a user interface, they may be provided with content-based information such as, but not limited to, information related to medical history, current or potential medical care providers, medical conditions, medications, nutritional supplements, advice or suggestions regarding diet and/or exercise, or any other type of information that may be considered relevant to the one or more users.

In one embodiment, the content-based information may be provided solely in a text format, however in various other embodiments, a user may also be presented with images that accompany the text, for example, images that depict one or more visual symptoms related to the user's medical conditions. The user may further be presented with graphical content, such charts, graphs, digital simulations, or other visualization tools. As one illustrative example, a user might be presented with a chart or graph that compares the user's symptoms with those of other patients diagnosed with the same or similar conditions. The user may further be presented with audio and/or video information related to their medical conditions. As additional illustrative examples, the user may be provided with one or more instructional videos that guide the user through physical therapy exercises, or educational videos that inform the user about the history and/or science behind their medical conditions. In various embodiments, the user may be presented with any combination of the above types of content-based information, or any other additional types of content that may be relevant to the particular user.

In addition to the types of content-based information discussed above, another type of information that may be provided to the one or more users is aesthetics-based information. This type of information may not be immediately recognized by a user, but it nevertheless plays an important role in the way in which the user absorbs and reacts to the presentation of the content-based information. This aesthetics-based information is used to create the overall user experience that is provided to a user by an application, and thus may also be referred to herein as user experience information, or user experience data. Examples of user experience data include, but are not limited to, the colors and fonts used to present the content-based information to a user, the various shapes of the graphical user interface elements, the layout or ordering of the content-based information presented to a user, and/or the sound effects, music, or other audio elements that may accompany the presentation of or interaction with the content-based information.

In one embodiment, once the one or more users are provided with information through the user interface at 106, process flow proceeds to 108. At 108, the interactions of the one or more users with the information presented through the user interface are monitored and collective user interaction data is generated.

The interactions of one or more users with the information presented through the user interface may be monitored through collection of user input data received through the user interface. The user input data collected may include, but is not limited to, data associated with click-stream input, textual input, touch input, gesture input, audio input, image input, video input, accelerometer input, and/or physiological input. In one embodiment, once the user input data is collected from the one or more users, the user input data from each of the one or more users is processed and aggregated to generate collective user interaction data.

As one illustrative example, in one embodiment, a digital therapeutics application may be configured to monitor specific types of user interaction data, in order to enable further data analysis and processing. In one embodiment, the digital therapeutics application may be configured to monitor the speed at which one or more users interact with the information provided. In one embodiment, the speed at which a user interacts with the information provided may be measured by collecting clickstream data, which may include data such as how long a user spends engaging with various parts of the information content presented to the user.

For example, consider the situation where a user of a digital therapeutics application is presented with a lengthy article related to one or more of their medical conditions. In this example, the user would likely need to fully scroll through the content to read the entire article. The time it takes for a user to scroll from the top of the text to the bottom of the text may be determined from the user input data, and this input data could then be used to generate user interaction data representing the speed at which the user read, or interacted, with the article.

As a further example, a user of a digital therapeutics application may be presented with a series of screens, where each screen may contain one or more types of information related to the user's medical conditions. For instance, the first screen may include text and images, the second screen may include one or more graphical visualizations, and the third screen may include an audio/video presentation, along with textual information. Each screen may have user interface elements, such as navigation buttons, allowing the user to move forward and backwards between the different screens. The time it takes the user to click or touch from one screen to the next, or from the beginning to the end of the presentation may be determined from the user input data, and this input data could then also be used to generate user interaction data representing the speed at which the user read, or interacted with, the presentation.

Additionally, a user may be presented with a variety of questions or exercises requiring textual responses, and the frequency of the typing and deleting events could be used to generate user interaction data representing the speed at which the user interacted with the exercise materials.

In another embodiment, the digital therapeutics application may be configured to monitor one or more users' interactions with the information to determine the one or more users' level of comprehension with respect to that information. In one embodiment, the level of comprehension associated with a user and the information provided to the user may be measured by periodically presenting the user with a variety of prompts or questions designed to determine whether the user is engaged with and understanding the information being presented. A comprehension level may then be calculated, for example, based on the percentage of questions that the user answered correctly.

Further, in one embodiment, a user's level of comprehension may be determined based on the percentage of the provided information that the user read or interacted with. For example, if a user begins reading an article, but the user input data indicates that the user never scrolls to the end of the article, it may be determined that the user has poor comprehension of the information provided. Likewise, in the case where a user is presented with multiple screens of information, for example, ten screens, if the user only navigates to two of the ten screens, then it may be determined that the user has poor comprehension of the information provided.

It should be noted here, that the foregoing examples are given for illustrative purposes only, and are not intended to limit the scope of the invention as disclosed herein and as claimed below.

In one embodiment, once the interactions of the one or more users with the information presented through the user interface are monitored and the associated collective user interaction data is generated at 108, process flow proceeds to 110. In one embodiment, at 110, the collective user interaction data is analyzed, and average user interaction data is generated.

As discussed above, in various embodiments, the collective user interaction data may include, but is not limited to, data generated based on associated click-stream input, textual input, touch input, gesture input, audio input, input, video input, accelerometer input, and/or physiological input obtained through monitoring of the interactions of one or more users with the information provided through the user interface.

In one embodiment, at 110, the collective user interaction data is analyzed to determine averages across the one or more users with respect to individual types of user interaction data. For example, types of user interaction data may include, but are not limited to, the number of times a user accesses the application, the length of time a user spends engaging with the application, how long a user has had access to the application, the type of information that a user engages with the most while using the application, whether or not a user utilizes advanced input mechanisms, the type of input mechanisms most preferred by a user, the speed at which a user engages with the information presented through the application, and the level of comprehension a user has of the information presented through the application.

Consider the above described illustrative example, in which a digital therapeutics application is configured to monitor the speed at which one or more users engage with the information presented through the user interface, as well the level of comprehension one or more users have of the information presented through the user interface. In this specific illustrative example, at 110, the collective user interaction data would include data indicating the speed at which each of the one or more users interacts with the information presented, as well as data indicating the level of comprehension that each of the one or more users has with respect to the information presented. Each of the one or more users may have multiple associated data points that form part of the collective user interaction data. For example, one user may have a particular interaction speed and/or comprehension level associated with a particular piece of information, received on a particular day. The same user may have a different interaction speed and/or comprehension level associated with the same piece of information, received on a different day, etc. Further, it may be considered desirable for the digital therapeutics application to group the collective user data based on user characteristics such as, but not limited to, age, gender, race, or type of medical condition. Thus, the digital therapeutics application may be configured to consider a wide variety of factors when analyzing the collective user interaction data to generate average user interaction data.

As one simplified illustrative example, the digital therapeutics application may be configured to analyze the collective user interaction data to calculate an average speed of interaction with a particular article of information among all female users, aged 55-65, who have been diagnosed with breast cancer. The application may further be configured to calculate an average level of comprehension of video content among all male users, aged 65-75, who have been diagnosed with Alzheimer's disease. It should be readily apparent from the above illustrative examples that a vast number of configuration options would be available to determine averages among users of the application, and the specific configurations would depend upon the goals of the application administrators. As such, it should again be noted here, that the foregoing examples are given for illustrative purposes only, and are not intended to limit the scope of the invention as disclosed herein.

In one embodiment, once the collective user interaction data is analyzed and average user interaction data is generated at 110, process flow proceeds to 112. In one embodiment, at 112, one or more threshold user interaction differentials are defined and utilized to generate threshold user interaction differential data.

In one embodiment, one or more threshold user interaction differentials are defined, such that users whose user interaction data varies from the average user interaction data can be identified. In one embodiment, a threshold user interaction differential represents a maximum allowable variation between a specific user's interaction data and the average user interaction data. In various embodiments, the threshold user interaction differential may be defined in various ways, such as, but not limited to, through application configuration options, or use of a predetermined standard.

Continuing the example of the digital therapeutics application, in one embodiment, after generation of the average user interaction data, it may be determined that the average level of comprehension of video content among male users, aged 65-75, who have been diagnosed with Alzheimer's disease is 50%, where 50% represents the percentage of comprehension questions related to video content that were correctly answered by the patients in this particular group. It may be decided by specialists, or other health care professionals, that a 10% variance is relatively common, and as such, patients in this group whose user interaction data indicated a 40% comprehension level with respect to video content would not raise concerns. However, if the threshold user interaction differential were defined at 20% variance, then patients in this group whose user interaction data indicated a 29% comprehension level with respect to video content would raise concerns, and further action might be deemed appropriate, as will be discussed in further detail below.

As already noted above, in various embodiments, a large number of individual possible averages may be generated during the generation of the average user interaction data at 110, depending on the various groupings of users and user interaction data types, and as such, it follows from the preceding discussion that there could potentially be a different threshold user interaction differential associated with each of the individual averages that form the average user interaction data. In one embodiment, this collection of threshold user interaction differentials is aggregated to generate threshold user interaction differential data.

In one embodiment, once one or more threshold user interaction differentials are defined and utilized to generate threshold user interaction differential data at 112, process flow proceeds to 114. In one embodiment, at 114, a current user of the application is provided with information through the user interface of the application.

In contrast to operation 106 described above, where one or more users are provided with information through the application user interface, at 114, a single specific user is provided with information through the user interface of the application, during a single current session of using the application. Therefore, the single specific user may hereafter be referred to as the current user.

As described in detail above, with respect to information provided to one or more users, in various embodiments, the information provided to the current user through the user interface includes, but is not limited to, textual information, audio information, graphical information, image information, video information, user experience information, and/or any combination thereof. In one embodiment, the information is provided to the current user in such a way that allows the current user to interact with the information provided.

In one embodiment, once information is provided to a current user at 114, process flow proceeds to 116. In contrast to operation 108 described above, where one or more users' interactions with the information provided through the user interface are monitored to generate collective user interaction data, at 116, the current user's interactions with the information provided through the user interface are monitored to generate current user interaction data.

As described in detail above, with respect to monitoring the interactions of one or more users to generate collective user interaction data, in various embodiments, the interactions of the current user with the information presented through the user interface may be monitored through collection of user input data received through the user interface. The user input data collected may include, but is not limited to, data associated with click-stream input, textual input, touch input, gesture input, audio input, image input, video input, accelerometer input, and/or physiological input. In one embodiment, once the user input data is collected from the current user, the user input data is processed and aggregated to generate current user interaction data.

As also described in detail above, with respect to monitoring the interactions of one or more users to generate collective user interaction data, in various embodiments, the application may be configured to monitor specific types of current user interaction data, such as, but not limited to, the speed at which the current user interacts with the information provided, and/or the current user's level of comprehension with respect to the information provided. In one embodiment, the speed at which the current user interacts with the information provided may be measured by collecting clickstream data, which may include data such as how long the current user spends engaging with various parts of the information content presented to the current user through the user interface. In one embodiment, the level of comprehension associated with the current user and the information provided may be measured by periodically presenting the current user with a variety of prompts or questions designed to determine whether the current user is engaged with and understanding the information being presented. A comprehension level may then be calculated, for example, based on the percentage of questions that the current user answered correctly. Further, in one embodiment, the current user's level of comprehension may be determined based on the percentage of the provided information that the current user read or interacted with.

In one embodiment, once the current user's interactions with the information provided through the user interface are monitored to generate current user interaction data at 116, process flow proceeds to 118. In one embodiment, at 118, the current user interaction data is analyzed along with the average user interaction data, to generate current user interaction differential data, which represents any differential between the current user interaction data and the average user interaction data.

In one embodiment, the current user interaction data is analyzed to extract the data that is most relevant to the type of user interaction data the application has been configured to monitor. For example, if the application has been configured to monitor user interaction speed and user comprehension level, then data related to the current user's interaction speed and the current user's comprehension level is extracted from the current user interaction data.

In one embodiment, once the relevant user interaction data has been extracted from the current user interaction data, the average user interaction data is analyzed to determine the data in the average user interaction data that corresponds to the relevant user interaction data. The current user interaction data is then compared to the corresponding data in the average user interaction data to determine whether there is any differential between the current user interaction data and the corresponding data in the average user interaction data, and current user interaction differential data is generated, which represents any such differential between the current user interaction data and the corresponding data in the average user interaction data.

Returning to the illustrative example of the digital therapeutics application described above, if the current user is a female, aged 60, who has been diagnosed with breast cancer, and the relevant user interaction data is data associated with speed of interaction, then the average user interaction data would be analyzed to extract the data that provides the average speed of interaction of females aged 55 to 65, who have been diagnosed with breast cancer. If, for example, the current user interaction speed is measured to be 150 words per minute, and the corresponding average interaction speed is 200 words per minute, then the differential between the current user interaction speed and the corresponding average interaction speed would be 50 words per minute, and this value would be represented by the current user interaction differential data. In various embodiments, the current user interaction differential data includes differential data related to multiple types of user interaction data. For example, the current user interaction differential data may include, but is not limited to, differential data related to current user speed of interaction, as well as differential data related to current user comprehension level.

As already noted several times above, the foregoing examples are given for illustrative purposes only, and are not intended to limit the scope of the invention as disclosed herein and as claimed below. As one example, user interaction speed may be measured using any means of measurement available, and should not be construed herein as limited to a measurement requiring words per minute.

In one embodiment, once the current user interaction data is analyzed along with the average user interaction data to generate current user interaction differential data at 118, process flow proceeds to 120. At 120, the current user interaction differential data for one or more types of user interaction data is compared with the threshold user interaction differential data corresponding to the same one or more types of user interaction data to determine whether one or more of the current user interaction differentials is greater than the corresponding threshold user interaction differentials.

For example, in one embodiment, the current user interaction differential associated with user interaction speed may be compared to the threshold user interaction differential associated with user interaction speed, and the current user interaction differential associated with user comprehension level may be compared to the threshold user interaction differential associated with user comprehension level. In this example, the comparison may yield that none, one, or both of the user interaction differentials is greater than their corresponding threshold user interaction differentials.

In one embodiment, once the current user interaction differential data is compared with the threshold user interaction differential data at 120, process flow proceeds to 122. At 122, if one or more of the current user interaction differentials is greater than the corresponding threshold user interaction differentials, it may be determined that this is indicative of an anomaly in the psychological state of the user, and this data may be utilized to arrive at one or more predictions regarding the current user's mental state. Upon identifying the current user's mental state and/or identifying anomalies in the user's mental state, one or more actions may be taken.

In one embodiment, the actions to be taken may be determined based on the severity of any anomaly. For example, if the anomaly is minor, then actions might be taken to make minor adjustments to the information content data and/or the user experience data that is presented to the current user. On the other hand, if the anomaly is severe, then actions might be taken to make major adjustments to the information content data and/or the user experience data that is presented to the current user. In one embodiment, adjustments to the information content data may include adjustments such as, but not limited to, providing textual content that uses gentler language, providing audio content that includes quieter, more relaxing voices, sounds, or music, or providing image/video content that is less realistic or less graphic. Adjustments to the user experience data may include adjustments such as, but not limited to, changing the colors, fonts, shapes, presentation, and/or layout of the information content data presented to the current user.

For example, in one embodiment, as discussed above, the application is a digital therapeutics application, and the current user is a patient who has been diagnosed with a medical condition. Many patients experience a great deal of anxiety related to their medical conditions. If an anomaly is detected in the psychological state of the current user, this may indicate that the current user is experiencing a higher than normal level of anxiety, and therefore may benefit from assistance, or from adjustments designed to reduce the current user's anxiety level.

As one specific illustrative example, if a determination is made that the current user is slightly more anxious than a corresponding average user, minor actions may be taken to reduce the current user's anxiety level, such as adjusting the content and/or presentation of the information that is being provided to the current user through the user interface. As one simplified illustrative example, cool colors such as blue and violet are known to produce calming effects, and rounder, softer shapes are also associated with calming effects. So in this situation, the user experience content data may be modified so that the content is presented to the user with a blue/violet color scheme, and the graphical user elements may be changed to include rounder and softer shapes. As another specific illustrative example, if a determination is made that the current user is significantly more anxious than a corresponding average user, more extreme actions may be taken, such as notifying one or more medical professionals associated with the user through a notification system of the application, or some other form of personal intervention from one or more medical professionals associated with the current user.

In various embodiments several additional types of actions may be appropriate specifically when dealing with users who have been diagnosed with a medical condition, such as, but not limited to: asking the user for input and/or response data; alerting the user; alerting one or more of the user's mental health or medical professionals; making notes in, adding data to, or highlighting the user's electronic file; making a specialist referral; recommending support contacts to the user; prescribing additional appointments, treatments, actions, or medications; calling emergency response or intervention professionals; notifying emergency contacts, relatives, or caregivers, etc.

In one embodiment, once one or more actions are taken based on the current user interaction data at 122, process flow proceeds to END 124 and the process 100 for remotely identifying and monitoring anomalies in the psychological state of application users based on analysis of average user interaction data and current user interaction data is exited to await new data and/or instructions.

Figure 2:
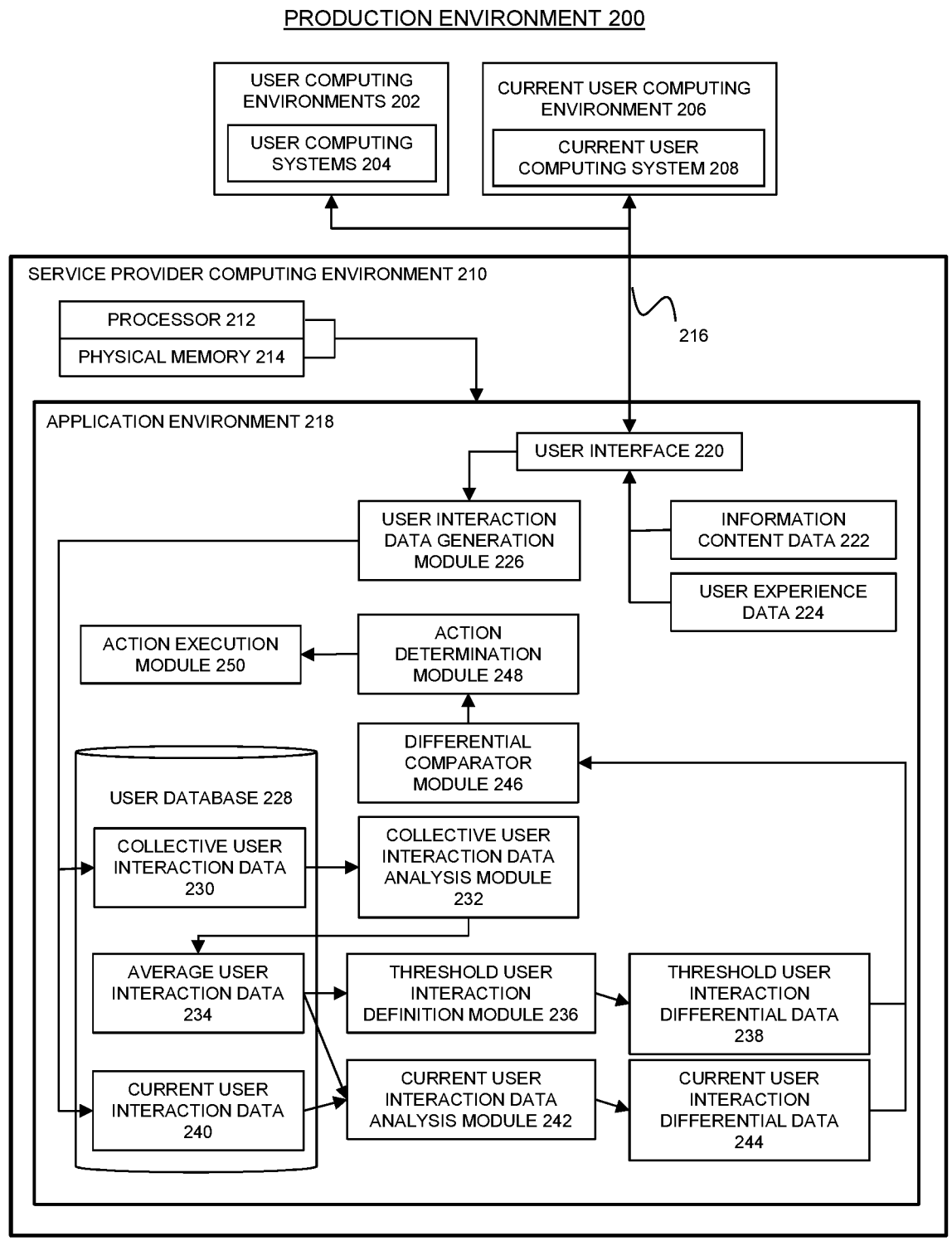
FIG. 2 is a block diagram of a production environment for remotely identifying and monitoring anomalies in the psychological state of application users based on analysis of average user interaction data and current user interaction data in accordance with a first embodiment.

FIG. 2 is a block diagram of a production environment 200 for remotely identifying and monitoring anomalies in the psychological state of application users based on analysis of average user interaction data and current user interaction data in accordance with a first embodiment.

In one embodiment, production environment 200 includes user computing environments 202, current user computing environment 206, and service provider computing environment 210. User computing environments 202 and current user computing environment 206 further comprise user computing systems 204 and current user computing system 208, respectively. The computing environments 202, 206, and 210 are communicatively coupled to each other with one or more communication networks 216.

In one embodiment, service provider computing environment 210 includes processor 212, physical memory 214, and application environment 218. Processor 212 and physical memory 214 coordinate the operation and interaction of the data and data processing modules associated with application environment 218. In one embodiment, application environment 218 includes user interface 220, which is provided to user computing systems 204 and user computing system 208 through the one or more communication networks 216.

In one embodiment, application environment 218 further includes user interaction data generation module 226, collective user interaction data analysis module 232, threshold user interaction definition module 236, current user interaction data analysis module 242, differential comparator module 246, action determination module 248, and action execution module 250, each of which will be discussed in further detail below.

Additionally, in one embodiment, application environment 218 includes information content data 222, user experience data 224, collective user interaction data 230, average user interaction data 234, threshold user interaction differential data 238, current user interaction data 240, and current user interaction differential data 244, each of which will be discussed in further detail below. In some embodiments, collective user interaction data 230, average user interaction data 234, and current user interaction data 240 may be stored in user database 228, which includes data associated with one or more users of application environment 218.

In one embodiment, user computing systems 204 of user computing environments 202, which are associated with one or more users of application environment 218, are provided with a user interface 220, which allows the one or more users to receive output from the application environment 218, as well as to provide input to the application environment 218, through the one or more communication networks 216.

As discussed above, in various embodiments, the application environment 218 may be any type of application environment that is capable of providing a user interface and content/information to a user, including, but not limited to, a desktop computing system application, a mobile computing system application, a virtual reality computing system application, an application provided by an Internet of Things (IoT) device, or any combination thereof. Further, in various embodiments, the user interface 220 may include any combination of a graphical user interface, an audio-based user interface, a touch-based user interface, or any other type of user interface currently known to those of skill in the art, or any other type of user interface that may be developed after the time of filing.

In one embodiment, user computing systems 204 of user computing environments 202, which are associated with one or more users of application environment 218, are provided with information content data 222 and user experience data 224 through the user interface 220.

In various embodiments, the information content data 222 provided to the one or more users through the user interface 220 includes, but is not limited to, textual information, audio information, graphical information, image information, video information, and/or any combination thereof. In one embodiment, the information content data 222 is provided to the one or more users in such a way that allows the one or more users to interact with the information content data 222.

In various embodiments, the user experience data 224 includes, but is not limited to, colors and fonts used to present the information content data 222 to a user, the various shapes of graphical user interface elements, the layout or ordering of the information content data 222, and/or the sound effects, music, or other audio elements that may accompany the presentation of or interaction with the information content data 222.

In one embodiment, once the one or more users are provided with information content data 222 and user experience data 224 through the user interface 220, the interactions of the one or more users with the information content data 222 are monitored by user interaction data generation module 226 through collection of user input data received through the user interface 220. The user input data collected by user interaction data generation module 226 may include, but is not limited to, data associated with click-stream input, textual input, touch input, gesture input, audio input, image input, video input, accelerometer input, and/or physiological input. In one embodiment, once the user input data is collected by user interaction data generation module 226, the user input data from each of the one or more users is processed and aggregated by user interaction data generation module 226 to generate collective user interaction data 230.

In various embodiments, user interaction data may include data such as, but not limited to, the number of times a user accesses the application environment 218, the length of time a user spends engaging with the application environment 218, how long a user has had access to the application environment 218, the type of information content data 222 that a user engages with the most while using the application environment 218, whether or not a user utilizes advanced input mechanisms that may be provided by user interface 220, the type of input mechanisms most preferred by a user, the speed at which a user interacts with the information content data 222 presented through the user interface 220, and the level of comprehension a user has of the information content data 222 presented through the user interface 220.

In one embodiment, once collective user interaction data 230 has been generated by user interaction data generation module 226, the collective user interaction data 230 is analyzed by collective user interaction data analysis module 232 to generate average user interaction data 234.

In one embodiment, collective user interaction data analysis module 232 analyzes collective user interaction data 230 to determine averages across one or more users or one or more groups of users with respect to the individual types of user interaction data that form the collective user interaction data 230. As noted above, examples of individual types of user interaction data may include user interaction data such as user interaction speed and user comprehension level. Further, each of the one or more users may have multiple data points associated with each type of user interaction data. In addition, application environment 218 may be configured to group the collective user interaction data 230 based on user characteristics such as, but not limited to, age, gender, and race. The collective user interaction data 230 may therefore be divided into any number of groups and each of the groups may be considered individually, as a whole, or in any desired combination, in order to generate average user interaction data 234.

In one embodiment, once the collective user interaction data 230 is analyzed by collective user interaction data analysis module 232 and average user interaction data 234 is generated, the average user interaction data 234 is utilized by threshold user interaction definition module 236 to define one or more threshold user interaction differentials, such that users whose user interaction data varies from the average user interaction data 234 can be identified. In one embodiment, a threshold user interaction differential represents a maximum allowable variation between a specific user's interaction data and the average user interaction data. In various embodiments, the threshold user interaction differential may be defined in various ways, such as, but not limited to, through application configuration options, or use of a predetermined standard.

As already noted above, in various embodiments, a large number of individual possible averages may be generated during the generation of the average user interaction data 234, depending on the various groupings of users and user interaction data types, and as such, it follows that there could potentially be a different threshold user interaction differential associated with each of the averages that make up average user interaction data 234. In one embodiment, this collection of threshold user interaction differentials is aggregated by threshold user interaction definition module 236 to generate threshold user interaction differential data 238.

In one embodiment, once threshold user interaction differential data 238 is generated by threshold user interaction definition module 236, current user computing system 208 of user computing environment 206, which is associated with a current user of application environment 218, is provided with information content data 222 and user experience data 224 through the user interface 220.

In one embodiment, once the current user is provided with information content data 222 and user experience data 224 through the user interface 220, the interactions of the current user with the information content data 222 are monitored by user interaction data generation module 226 through collection of user input data received through the user interface 220. The user input data collected by user interaction data generation module 226 may include, but is not limited to, data associated with click-stream input, textual input, touch input, gesture input, audio input, image input, video input, accelerometer input, and/or physiological input. In one embodiment, once the current user input data is collected by user interaction data generation module 226, the current user input data is processed and aggregated by user interaction data generation module 226 to generate current user interaction data 240.

In one embodiment, once current user interaction data 240 has been generated by user interaction data generation module 226, the current user interaction data 240 is analyzed along with the average user interaction data 234, to generate current user interaction differential data 244, which represents any differential between the current user interaction data 240 and the average user interaction data 234.

In one embodiment, the current user interaction data 240 is analyzed to extract the data that is most relevant to the type of user interaction data the application environment 218 has been configured to monitor. For example, if the application environment 218 has been configured to monitor user interaction speed and user comprehension level, then data related to the current user's interaction speed and the current user's comprehension level is extracted from the current user interaction data 240.

In one embodiment, once the relevant user interaction data has been extracted from the current user interaction data 240, the average user interaction data 234 is analyzed to determine the data in the average user interaction data 234 that corresponds to the relevant user interaction data. The current user interaction data 240 is then compared to the corresponding data in the average user interaction data 234 to determine whether there is any differential between the current user interaction data 240 and the corresponding data in the average user interaction data 234. Current user interaction data analysis module 242 then generates current user interaction differential data 244, which represents any such differential between the current user interaction data 240 and the corresponding data in the average user interaction data 234.

In one embodiment, once the current user interaction data 240 is analyzed along with the average user interaction data 234 to generate current user interaction differential data 244, differential comparator module 246 compares the current user interaction differential data 244 for one or more types of user interaction data with the threshold user interaction differential data 238 corresponding to the same one or more types of user interaction data to determine whether one or more of the current user interaction differentials in current user interaction differential data 244 is greater than the corresponding threshold user interaction differentials in threshold user interaction differential data 238.

For example, in one embodiment, the current user interaction differential associated with user interaction speed may be compared to the threshold interaction differential associated with user interaction speed, and the current user interaction differential associated with user comprehension level may be compared to the threshold interaction differential associated with user comprehension level. In this example, the comparison may yield that none, one, or both of the user interaction differentials is greater than their corresponding threshold interaction differentials.

In one embodiment, once the current user interaction differential data 244 is compared with the threshold interaction differential data 238, if one or more of the current user interaction differentials is found, by differential comparator module 246, to be greater than the corresponding threshold interaction differentials, it may be determined that this is indicative of an anomaly in the psychological state of the user, and one or more actions may be taken, as determined by action determination module 248.

In one embodiment, the actions to be taken may be determined by action determination module 248 based on the severity of the anomaly. For example, if the anomaly is minor, then action determination module 248 may determine that actions should be taken to make slight adjustments to the information content data 222 and/or the user experience data 224 that is presented to the current user through the user interface 220. On the other hand, if the anomaly is severe, then action determination module 248 may determine that actions should be taken to make major adjustments to the information content data 222 and/or the user experience data 224 that is presented to the current user through the user interface 220. In other embodiments, action determination module 248 may determine that more extreme actions should be taken. For example, if a current user is determined to be in a severely anxious mental state, action determination module 248 may determine that actions such as emergency notifications and personal intervention are appropriate.

In various embodiments, once action determination module 248 determines actions to be taken, control proceeds to action execution module 250 for execution of the determined actions. Action execution may include, for example, selecting and providing different information content data 222 or user experience data 224 that is more appropriate for the current user's psychological state, contacting the user through any user approved contact means, and/or contacting a user's trusted third party on behalf of the user.

Figure 3:
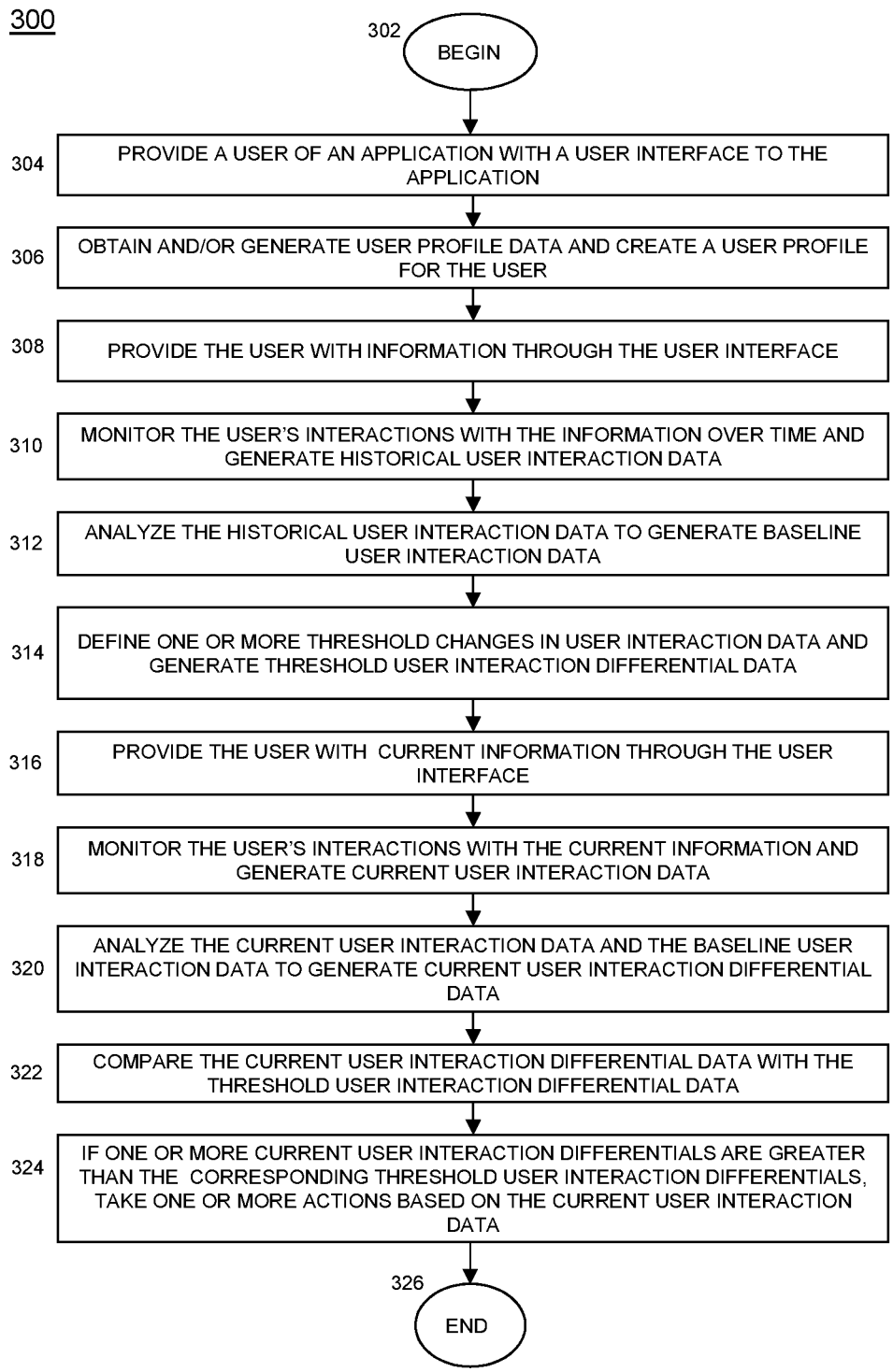
FIG. 3 is a flow chart of a process for remotely identifying and monitoring changes or anomalies in the psychological state of application users based on historical user interaction data and current user interaction data in accordance with a second embodiment.

FIG. 3 is a flow chart of a process 300 for remotely identifying and monitoring changes or anomalies in the psychological state of application users based on historical user interaction data and current user interaction data in accordance with a second embodiment.

Process 300 begins at BEGIN 302 and process flow proceeds to 304. At 304, a user of an application is provided with a user interface, which allows the user to receive output from the application, as well as to provide input to the application.

In various embodiments, the application may be any type of application that is capable of providing content/information to a user through a user interface, including, but not limited to, a desktop computing system application, a mobile computing system application, a virtual reality computing system application, an application provided by an Internet of Things (IoT) device, or any combination thereof. In various embodiments, the user interface may include any combination of a graphical user interface, an audio-based user interface, a touch-based user interface, or any other type of user interface currently known to those of skill in the art, or any other type of user interface that may be developed after the time of filing.

In one embodiment, the application provided to the user is a digital therapeutics application, which is designed to assist patients who have been diagnosed with one or more medical conditions. As a specific illustrative example, upon diagnosing a patient with one or more medical conditions, a medical care professional may prescribe the patient access to the digital therapeutics application. The digital therapeutics application may be accessed by the patient through any type of computing system that is capable of providing a user interface to a user, as discussed above. Upon accessing the digital therapeutics application, the patient then becomes a user of the application, and is provided with a user interface, which enables the user to interact with the digital therapeutics application.

In one embodiment, once the user is provided with a user interface to the application at 304, process flow proceeds to 306. In one embodiment, at 306, user profile data is obtained and/or generated and a user profile is created for the user.

In some embodiments, the user profile may contain data such as, but not limited to, the user's name, age, date of birth, gender, race, and/or occupation. The user profile may further contain data related to the user's individual sessions with the application, or data related to the user's interactions with the application over time. In the example of a digital therapeutics application, in some embodiments, the user profile may contain information specific to the application's field of use, such as the user's medical history, medical conditions, medications, and/or medical care providers.

In some embodiments, the user profile may be made accessible to the user, and the user may be given permissions to view and modify one or more parts of the profile. In other embodiments, the user profile is not made accessible to the user, and is instead maintained solely for use by the application and/or the application administrators. In other embodiments, the user profile is not made accessible to the user, and is instead accessible only by third parties, such as one or more medical professionals. In some embodiments, some parts of the user profile may be made accessible to the user or third parties, while other parts of the user profile may be inaccessible by the user or third parties.

In one embodiment, once a user profile is created for the user at 306, process flow proceeds to 308. At 308, the user is provided with information through the user interface.

In various embodiments, the information provided to the user through the user interface includes, but is not limited to, textual information, audio information, graphical information, image information, video information, and/or any combination thereof. In one embodiment, the information is provided to the user in such a way that allows the user to interact with the information provided. For example, the user may be presented with information on the screen of an electronic device, along with a variety of graphical user elements, which allow the user to scroll through the information, click on buttons associated with the information, and/or enter textual strings in response to the information. When the information is presented to the user on a device that includes a touch screen, the interaction may include touch-based interactions and/or gesture recognition. In addition to textual inputs and touch or click-based inputs, in various embodiments, the user may be able to interact with the information through more advanced input mechanisms such as through audio input, video input, accelerometer input, voice recognition, facial recognition or through a variety of physiological sensors. Examples of physiological sensors may include, but are not limited to, heart rate monitors, blood pressure monitors, eye tracking monitors, or muscle activity monitors.

As one specific illustrative example, in one embodiment, once a user of a digital therapeutics application is provided with a user interface, they may be provided with content-based information such as, but not limited to, information related to medical history, current or potential medical care providers, medical conditions, medications, nutritional supplements, advice or suggestions regarding diet and/or exercise, or any other type of information that may be considered relevant to the user.

In one embodiment, the content-based information may be provided solely in a text format, however in various other embodiments, the user may also be presented with images that accompany the text, for example, images that depict one or more visual symptoms related to the user's medical conditions. The user may further be presented with graphical content, such charts, graphs, digital simulations, or other visualization tools. As one illustrative example, the user might be presented with a chart or graph that compares the user's symptoms with those of other patients diagnosed with the same or similar conditions. The user may further be presented with audio and/or video information related to their medical conditions. As additional illustrative examples, the user may be provided with one or more instructional videos that guide the user through physical therapy exercises, or educational videos that inform the user about the history and/or science behind their medical conditions. In various embodiments, the user may be presented with any combination of the above types of content-based information, or any other additional types of content that may be relevant to the user.

In addition to the types of content-based information discussed above, another type of information that may be provided to the user is aesthetics-based information. This type of information may not be immediately recognized by the user, but it nevertheless plays an important role in the way in which the user absorbs and reacts to the presentation of the content-based information. This aesthetics-based information is used to create the overall user experience that is provided to a user by an application, and thus may also be referred to herein as user experience information, or user experience data. Examples of user experience data include, but are not limited to, the colors and fonts used to present the content-based information to a user, the various shapes of the graphical user interface elements, the layout or ordering of the content-based information presented to a user, and/or the sound effects, music, or other audio elements that may accompany the presentation of or interaction with the content-based information.

In one embodiment, once the user is provided with information through the user interface at 308, process flow proceeds to 310. At 310, the interactions of the user with the information presented through the user interface are monitored over time and historical user interaction data is generated.

The interactions of the user with the information presented through the user interface may be monitored through collection of user input data received through the user interface. The user input data collected may include, but is not limited to, data associated with click-stream input, textual input, touch input, gesture input, audio input, image input, video input, accelerometer input, and/or physiological input.

In one embodiment, the user input data is collected and monitored over time, on a per-session basis. For example, a user may access and interact with the application several times per day, once per day, once per week, etc., and each instance of access and interaction would constitute an application session. In one embodiment, each time the user engages in an application session, the user input data is collected, and may be stored as part of the user profile. Further, in one embodiment, each time the user input data is collected from the user for an application session, the user input data from each of the previous sessions is processed and aggregated to generate historical user interaction data.

As one illustrative example, in one embodiment, a digital therapeutics application may be configured to monitor specific types of user interaction data, in order to enable further data analysis and processing. In one embodiment, the digital therapeutics application may be configured to monitor the speed at which a user interacts with the information provided. In one embodiment, the speed at which the user interacts with the information provided may be measured by collecting clickstream data, which may include data such as how long the user spends engaging with various parts of the information content presented to the user.

For example, consider the situation where a user of a digital therapeutics application is presented with a lengthy article related to one or more of their medical conditions. In this example, the user would likely need to fully scroll through the content to read the entire article. The time it takes for a user to scroll from the top of the text to the bottom of the text may be determined from the user input data, and this input data could then be used to generate user interaction data representing the speed at which the user read, or interacted, with the article. The user interaction data representing speed of interaction for this user, for this session, may then be stored as part of the user profile and/or included as part of the user's historical user interaction data.

As a further example, a user of a digital therapeutics application may be presented with a series of screens, where each screen may contain one or more types of information related to the user's medical conditions. For instance, the first screen may include text and images, the second screen may include one or more graphical visualizations, and the third screen may include an audio/video presentation, along with textual information. Each screen may have user interface elements, such as navigation buttons, allowing the user to move forward and backwards between the different screens. The time it takes the user to click or touch from one screen to the next, or from the beginning to the end of the presentation may be determined from the user input data, and this input data could then also be used to generate user interaction data representing the speed at which the user read, or interacted with, the presentation. Additionally, a user may be presented with a variety of questions or exercises requiring textual responses, and the frequency of the typing and deleting events could be used to generate user interaction data representing the speed at which the user interacted with the exercise materials.

Again, the user interaction data representing speed of interaction for this user, for this session, may then be stored as part of the user profile and/or included as part of the user's historical user interaction data.

In another embodiment, the digital therapeutics application may be configured to monitor a user's interactions with the information to determine the user's level of comprehension with respect to that information. In one embodiment, the level of comprehension associated with the user and the information provided to the user may be measured by periodically presenting the user with a variety of prompts or questions designed to determine whether the user is engaged with and understanding the information being presented. A comprehension level may then be calculated, for example, based on the percentage of questions that the user answered correctly.

Further, in one embodiment, a user's level of comprehension may be determined based on the percentage of the provided information that the user read or interacted with. For example, if a user begins reading an article, but the user input data indicates that the user never scrolls to the end of the article, it may be determined that the user has poor comprehension of the information provided. Likewise, in the case where a user is presented with multiple screens of information, for example, ten screens, if the user only navigates to two of the ten screens, then it may be determined that the user has poor comprehension of the information provided. The user interaction data representing comprehension level for this user, for this session, may then be stored as part of the user profile and/or included as part of the user's historical user interaction data.

It should be noted here, that the foregoing examples are given for illustrative purposes only, and are not intended to limit the scope of the invention as disclosed herein and as claimed below.

In one embodiment, once the interactions of the user with the information presented through the user interface are monitored over time and the associated historical user interaction data is generated at 310, process flow proceeds to 312. In one embodiment, at 312, the historical user interaction data is analyzed, and baseline user interaction data is generated.

As discussed above, in various embodiments, the historical user interaction data may include, but is not limited to, data generated based on associated click-stream input, textual input, touch input, gesture input, audio input, image input, video input, accelerometer input, and/or physiological input obtained through monitoring of the interactions of the user with the information provided through the user interface over time.

In one embodiment, at 312, the historical user interaction data is analyzed to determine one or more user baselines, across one or more of the user's application sessions, with respect to individual types of user interaction data. For example, types of user interaction data may include, but are not limited to, the number of times a user accesses the application, the length of time a user spends engaging with the application, how long a user has had access to the application, the type of information that a user engages with the most while using the application, whether or not a user utilizes advanced input mechanisms, the type of input mechanisms most preferred by a user, the speed at which a user engages with the information presented through the application, and the level of comprehension a user has of the information presented through the application.

Consider the above described illustrative example, in which a digital therapeutics application is configured to monitor the speed at which a user engages with the information presented through the user interface, as well the level of comprehension a user has of the information presented through the user interface. In this specific illustrative example, at 312, the historical user interaction data would include data indicating the speed at which the user interacted with the information presented during each of the user's application sessions, as well as data indicating the level of comprehension that the user had with respect to the information presented during each of the user's application sessions. Thus, the user may have multiple associated data points that form part of the historical user interaction data. For example, the user may have a particular interaction speed and/or comprehension level associated with a particular piece of information, received on a particular day. The same user may have a different interaction speed and/or comprehension level associated with the same piece of information, received on a different day, etc. Further, it may be considered desirable for the digital therapeutics application to group the historical user data based, for example, on time segments. As such, the historical user data may be analyzed for various time periods, such as the past week, the past month, the past year, etc. Thus, the digital therapeutics application may be configured to consider a variety of factors when analyzing the historical user interaction data to generate baseline user interaction data.

As one simplified illustrative example, the digital therapeutics application may be configured to analyze the user's historical user interaction data to calculate the user's baseline speed of interaction with a particular set of informational content over the past month. The application may further be configured to calculate the user's baseline level of comprehension of a different set of informational content over the past year. The analysis may further be configured to ignore data points that fall outside of a predefined threshold when calculating the user's baseline. Each of the calculated baselines would then be aggregated to generate the baseline user interaction data for this particular user.

In one embodiment, once the historical user interaction data is analyzed and baseline user interaction data is generated at 312, process flow proceeds to 314. In one embodiment, at 314, one or more threshold changes in user interaction data are defined and threshold user interaction differential data is generated.

In one embodiment, one or more threshold changes in user interaction data are defined, such that when the user's current user interaction data varies from the user's baseline user interaction data, appropriate actions can be taken. In one embodiment, a threshold change in the user interaction data represents a maximum allowable variation between the user's current interaction data and the user's baseline interaction data. In various embodiments, the threshold change in user interaction data may be defined in various ways, such as, but not limited to, through application configuration options, or use of a predetermined standard.

For example, in one embodiment, after generation of baseline user interaction data for a user, it may be determined that the user's baseline level of comprehension of a particular type of informational content is 50%, where 50% represents the percentage of comprehension questions related to the content that were previously correctly answered by the user. It may be decided by specialists, or other experts in the field of use, that a 10% variance is relatively common, and as such, if the current user interaction data for this user indicated a 40% comprehension level with respect to this type of informational content, this would not raise concerns. However, if the threshold change in the user interaction data for this particular type of content was defined at 20% variance, then if the current user interaction data for this user indicated a 29% comprehension level with respect to this type of informational content, this would raise concerns, and further action might be deemed appropriate, as will be discussed in further detail below.

As already noted above, in various embodiments, multiple user baselines may be generated during the generation of the baseline user interaction data at 312, and as such, it follows from the preceding discussion that there could potentially be a different threshold change in user interaction data associated with each of the individual baselines that form the baseline user interaction data. In one embodiment, this collection of threshold changes in user interaction data is aggregated to generate threshold user interaction differential data.

In one embodiment, once one or more threshold changes in user interaction data are defined and threshold user interaction differential data is generated at 314, process flow proceeds to 316. In one embodiment, at 316, the user of the application is provided with current information through the user interface of the application.

In contrast to operation 308 described above, where the user is provided with information through the application user interface over time, at 316, the user is provided with information through the user interface of the application during a single current session of using the application. Therefore, the information provided to the user during this single current session may hereafter be referred to as current information.

As described in detail above, with respect to information provided to the user through the user interface, in various embodiments, the current information provided to the user through the user interface includes, but is not limited to, textual information, audio information, graphical information, image information, video information, user experience information, and/or any combination thereof. In one embodiment, the current information is provided to the user in such a way that allows the user to interact with the information provided.

In one embodiment, once current information is provided to the user at 316, process flow proceeds to 318. In contrast to operation 310 described above, where the user's interactions with the information provided through the user interface are monitored over time to generate historical user interaction data, at 318, the user's interactions with the current information provided through the user interface are monitored to generate current user interaction data.

As described in detail above, with respect to monitoring the interactions of the user over time to generate historical user interaction data, in various embodiments, the interactions of the user with the current information presented through the user interface may be monitored through collection of user input data received through the user interface. The user input data collected may include, but is not limited to, data associated with click-stream input, textual input, touch input, gesture input, audio input, image input, video input, accelerometer input, and/or physiological input. In one embodiment, once the user input data is collected from the user, the user input data is processed and aggregated to generate current user interaction data.

As also described in detail above, with respect to monitoring the interactions of the user over time to generate historical user interaction data, in various embodiments, the application may be configured to monitor specific types of user interaction data, such as, but not limited to, the speed at which the user interacts with the current information provided, and/or the user's level of comprehension with respect to the current information provided. In one embodiment, the speed at which the user interacts with the current information provided may be measured by collecting click-stream data, which may include data such as how long the user spends engaging with various parts of the current information content presented to the user through the user interface. In one embodiment, the level of comprehension associated with the user and the current information provided may be measured by periodically presenting the user with a variety of prompts or questions designed to determine whether the user is engaged with and understanding the current information being presented. A comprehension level may then be calculated, for example, based on the percentage of questions that the user answered correctly. Further, in one embodiment, the user's level of comprehension may be determined based on the percentage of the currently provided information that the user read or interacted with.

In one embodiment, once the user's interactions with the current information provided through the user interface are monitored to generate current user interaction data at 318, process flow proceeds to 320. In one embodiment, at 320, the current user interaction data is analyzed along with the baseline user interaction data, to generate current user interaction differential data, which represents any differential between the current user interaction data and the baseline user interaction data.

In one embodiment, the current user interaction data is analyzed to extract the data that is most relevant to the type of user interaction data the application has been configured to monitor. For example, if the application has been configured to monitor user interaction speed and user comprehension level, then data related to the user's speed of interaction with the current information and the user's level of comprehension of the current information is extracted from the current user interaction data.

In one embodiment, once the relevant user interaction data has been extracted from the current user interaction data, the baseline user interaction data is analyzed to determine the data in the baseline user interaction data that corresponds to the relevant user interaction data. The current user interaction data is then compared to the corresponding data in the baseline user interaction data to determine whether there is any differential between the current user interaction data and the corresponding data in the baseline user interaction data, and current user interaction differential data is generated, which represents any such differential between the current user interaction data and the corresponding data in the baseline user interaction data.

Returning to the illustrative example of the digital therapeutics application described above, if the relevant user interaction data is data associated with speed of interaction, then the user's baseline user interaction data would be analyzed to extract the data that provides the user's baseline interaction speed. If, for example, the user's interaction speed with respect to the current information is measured to be 150 words per minute, and the user's baseline interaction speed is 200 words per minute, then the differential between the user's interaction speed with respect to the current information and the user's baseline interaction speed would be 50 words per minute, and this value would be represented by the current user interaction differential data. In various embodiments, the current user interaction differential data includes differential data related to multiple types of user interaction data. For example, the current user interaction differential data may include, but is not limited to, differential data related to user's speed of interaction, as well as differential data related to the user's comprehension level.

As already noted several times above, the foregoing examples are given for illustrative purposes only, and are not intended to limit the scope of the invention as disclosed herein and as claimed below. As one example, user interaction speed may be measured using any means of measurement available, and should not be construed herein as limited to a measurement requiring words per minute.

In one embodiment, once the current user interaction data is analyzed along with the baseline user interaction data to generate current user interaction differential data at 320, process flow proceeds to 322. At 322, the current user interaction differential data for one or more types of user interaction data is compared with the threshold user interaction differential data corresponding to the same one or more types of user interaction data to determine whether one or more of the current user interaction differentials is greater than the corresponding threshold user interaction differentials.

For example, in one embodiment, the current user interaction differential associated with user interaction speed may be compared to the threshold user interaction differential associated with user interaction speed, and the current user interaction differential associated with user comprehension level may be compared to the threshold user interaction differential associated with user comprehension level. In this example, the comparison may yield that none, one, or both of the user interaction differentials is greater than their corresponding threshold user interaction differentials.

In one embodiment, once the current user interaction differential data is compared with the threshold user interaction differential data at 322, process flow proceeds to 324. At 324, if one or more of the current user interaction differentials is greater than the corresponding threshold user interaction differentials, it may be determined that this is indicative of a change or anomaly in the psychological state of the user, and this data may be utilized to arrive at one or more predictions regarding the current user's mental state. Upon identifying the current user's mental state and/or identifying changes or anomalies in the current user's mental state, one or more actions may be taken.

In one embodiment, the actions to be taken may be determined based on the severity of the anomaly. For example, if the anomaly is minor, then actions might be taken to make slight adjustments to the information content data and/or the user experience data that is presented to the user. On the other hand, if the anomaly is severe, then actions might be taken to make extreme adjustments to the information content data and/or the user experience data that is presented to the user. In one embodiment, adjustments to the information content data may include adjustments such as, but not limited to, providing textual content that uses gentler language, providing audio content that includes quieter, more relaxing voices, sounds, or music, or providing image/video content that is less realistic or less graphic. Adjustments to the user experience data may include adjustments such as, but not limited to, changing the colors, fonts, shapes, presentation, and/or layout of the information content data presented to the user.

For example, in one embodiment, as discussed above, the application is a digital therapeutics application, and the user is a patient who has been diagnosed with a medical condition. Many patients experience a great deal of anxiety related to their medical conditions. If an anomaly is detected in the psychological state of the user, this may indicate that the user is experiencing a higher than normal level of anxiety, and therefore may benefit from assistance, or from adjustments designed to reduce the user's anxiety level.

As one specific illustrative example, if a determination is made that the user is slightly more anxious than they usually are, minor actions may be taken to reduce the user's anxiety level, such as adjusting the content and/or presentation of the information that is being provided to the user through the user interface. As one simplified illustrative example, cool colors such as blue and violet are known to produce calming effects, and rounder, softer shapes are also associated with calming effects. So in this situation, the user experience content data may be modified so that the content is presented to the user with a blue/violet color scheme, and the graphical user elements may be changed to include rounder and softer shapes. As another specific illustrative example, if a determination is made that the user is significantly more anxious than they usually are, more extreme actions may be taken, such as notifying one or more medical professionals associated with the user through a notification system of the application, or some other form of personal intervention from one or more medical professionals associated with the user.

In various embodiments several additional types of actions may be appropriate specifically when dealing with users who have been diagnosed with a medical condition, such as, but not limited to: asking the user for input and/or response data; alerting the user; alerting one or more of the user's mental health or medical professionals; making notes in, adding data to, or highlighting the user's electronic file; making a specialist referral; recommending support contacts to the user; prescribing additional appointments, treatments, actions, or medications; calling emergency response or intervention professionals; notifying emergency contacts, relatives, or caregivers, etc.

In one embodiment, once one or more actions are taken based on the user interaction data at 324, process flow proceeds to END 326 and the process 300 for remotely identifying and monitoring changes or anomalies in the psychological state of application users based on historical user interaction data and current user interaction data is exited to await new data and/or instructions.

Figure 4:
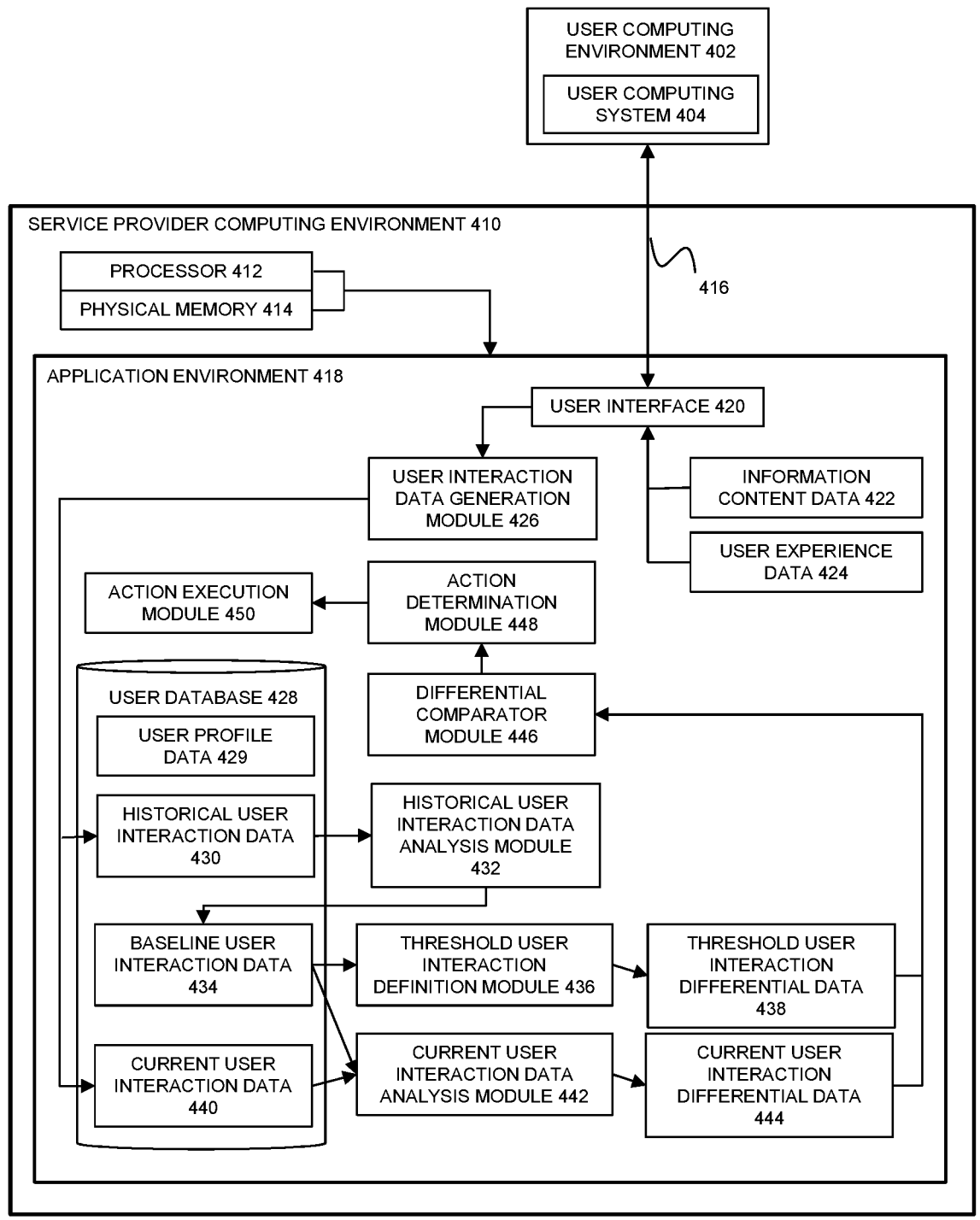
FIG. 4 is a block diagram of a production environment for remotely identifying and monitoring changes or anomalies in the psychological state of application users based on historical user interaction data and current user interaction data in accordance with a second embodiment.

FIG. 4 is a block diagram of a production environment 400 for remotely identifying and monitoring changes or anomalies in the psychological state of application users based on historical user interaction data and current user interaction data in accordance with a second embodiment.

In one embodiment, production environment 400 includes user computing environment 402, and service provider computing environment 410. User computing environment 402 further comprises user computing system 404. The computing environments 402 and 410 are communicatively coupled to each other with one or more communication networks 416.

In one embodiment, service provider computing environment 410 includes processor 412, physical memory 414, and application environment 418. Processor 412 and physical memory 414 coordinate the operation and interaction of the data and data processing modules associated with application environment 418. In one embodiment, application environment 418 includes user interface 420, which is provided to user computing system 404 through the one or more communication networks 416.

In one embodiment, application environment 418 further includes user interaction data generation module 426, historical user interaction data analysis module 432, threshold user interaction definition module 436, current user interaction data analysis module 442, differential comparator module 446, action determination module 448, and action execution module 450, each of which will be discussed in further detail below.

Additionally, in one embodiment, application environment 418 includes information content data 422, user experience data 424, user profile data 429, historical user interaction data 430, baseline user interaction data 434, threshold user interaction differential data 438, current user interaction data 440, and current user interaction differential data 444, each of which will be discussed in further detail below. In some embodiments, user profile data 429, historical user interaction data 430, baseline user interaction data 434, and current user interaction data 440 may be stored in user database 428, which includes data associated with one or more users of application environment 418.

In one embodiment, user computing system 404 of user computing environment 402, which is associated with a single user of application environment 418, is provided with a user interface 420, which allows the user to receive output from the application environment 418, as well as to provide input to the application environment 418, through the one or more communication networks 416.

As discussed above, in various embodiments, the application environment 418 may be any type of application environment that is capable of providing a user interface and content/information to a user, including, but not limited to, a desktop computing system application, a mobile computing system application, a virtual reality computing system application, an application provided by an Internet of Things (IoT) device, or any combination thereof. Further, in various embodiments, the user interface 420 may include any combination of a graphical user interface, an audio-based user interface, a touch-based user interface, or any other type of user interface currently known to those of skill in the art, or any other type of user interface that may be developed after the time of filing.

In one embodiment, once the user is provided with user interface 420, user profile data 429 is obtained and/or generated and a user profile is created for the user. In some embodiments, the user profile may contain data such as, but not limited to, the user's name, age, date of birth, gender, race, and/or occupation. The user profile may further contain data related to the user's individual sessions with the application environment 418, or data related to the user's interactions with the application environment 418 over time.

In one embodiment, once user profile data 429 is used to create a profile for the user, user computing system 404 of user computing environments 402, which is associated with a single user of application environment 418, is provided with information content data 422 and user experience data 424 through the user interface 420.

In various embodiments, the information content data 422 provided to the user through the user interface 420 includes, but is not limited to, textual information, audio information, graphical information, image information, video information, and/or any combination thereof. In one embodiment, the information content data 422 is provided to the user in such a way that allows the user to interact with the information content data 422.

In various embodiments, the user experience data 424 includes, but is not limited to, colors and fonts used to present the information content data 422 to the user, the various shapes of graphical user interface elements, the layout or ordering of the information content data 422, and/or the sound effects, music, or other audio elements that may accompany the presentation of or interaction with the information content data 422.

In one embodiment, once the user is provided with information content data 422 and user experience data 424 through the user interface 420, the interactions of the user with the information content data 422 are monitored over time by user interaction data generation module 426 through collection of user input data received through the user interface 420. The user input data collected by user interaction data generation module 426 may include, but is not limited to, data associated with click-stream input, textual input, touch input, gesture input, audio input, image input, video input, accelerometer input, and/or physiological input. In one embodiment, once the user input data is collected by user interaction data generation module 426, the user input data from each of the user's previous application sessions is processed and aggregated by user interaction data generation module 426 to generate historical user interaction data 430.

In various embodiments, user interaction data may include data such as, but not limited to, the number of times a user accesses the application environment 418, the length of time a user spends engaging with the application environment 418, how long a user has had access to the application environment 418, the type of information content data 422 that a user engages with the most while using the application environment 418, whether or not a user utilizes advanced input mechanisms that may be provided by user interface 420, the type of input mechanisms most preferred by a user, the speed at which a user interacts with the information content data 422 presented through the user interface 420, and the level of comprehension a user has of the information content data 422 presented through the user interface 420.

In one embodiment, once historical user interaction data 430 has been generated by user interaction data generation module 426, the historical user interaction data 430 is analyzed by historical user interaction data analysis module 432 to generate baseline user interaction data 434.

In one embodiment, historical user interaction data analysis module 432 analyzes historical user interaction data 430 to determine one or more user baselines, across one or more of the user's application sessions, with respect to the individual types of user interaction data that form the historical user interaction data 430. As noted above, examples of individual types of user interaction data may include user interaction data such as user interaction speed and user comprehension level. Further, the user may have multiple data points associated with each type of user interaction data. In addition, application environment 418 may be configured to group the historical user interaction data 430 based on factors, such as, but not limited to, time periods associated with the user interaction data. The historical user interaction data 430 may therefore be divided into any number of segments and each of the segments may be considered individually, as a whole, or in any desired combination, in order to generate baseline user interaction data 434.

In one embodiment, once the historical user interaction data 430 is analyzed by historical user interaction data analysis module 432 and baseline user interaction data 434 is generated, the baseline user interaction data 434 is utilized by threshold user interaction definition module 436 to define one or more threshold changes in user interaction data, such that when the user's current user interaction data 440 varies from the user's baseline user interaction data 434, appropriate actions can be taken. In one embodiment, a threshold change in user interaction data represents a maximum allowable variation between a user's current user interaction data 440 and the user's baseline user interaction data 434. In various embodiments, the threshold change in user interaction data may be defined in various ways, such as, but not limited to, through application configuration options, or use of a predetermined standard.

As already noted above, in various embodiments, multiple user baselines may be generated during the generation of the baseline user interaction data 434, and as such, it follows that there could potentially be a different threshold change in user interaction data associated with each of the individual baselines that form the baseline user interaction data 434. In one embodiment, this collection of threshold changes in user interaction data is aggregated by threshold user interaction definition module 436 to generate threshold user interaction differential data 438.

In one embodiment, once threshold user interaction differential data 438 is generated by threshold user interaction definition module 436, user computing system 404 of user computing environment 402, which is associated with a single user of application environment 418, is provided with current information content data 422 and current user experience data 424 through the user interface 420.

In one embodiment, once the user is provided with current information content data 422 and current user experience data 424 through the user interface 420, the interactions of the user with the current information content data 422 are monitored by user interaction data generation module 426 through collection of user input data received through the user interface 420. The user input data collected by user interaction data generation module 426 may include, but is not limited to, data associated with click-stream input, textual input, touch input, gesture input, audio input, image input, video input, accelerometer input, and/or physiological input. In one embodiment, once the current user input data is collected by user interaction data generation module 426, the current user input data is processed and aggregated by user interaction data generation module 426 to generate current user interaction data 440.

In one embodiment, once current user interaction data 440 has been generated by user interaction data generation module 426, the current user interaction data 440 is analyzed along with the baseline user interaction data 434, to generate current user interaction differential data 444, which represents any differential between the current user interaction data 440 and the baseline user interaction data 434.

In one embodiment, the current user interaction data 440 is analyzed to extract the data that is most relevant to the type of user interaction data the application environment 418 has been configured to monitor. For example, if the application environment 418 has been configured to monitor user interaction speed and user comprehension level, then data related to the user's speed of interaction with the current information content data 422 and the user's level of comprehension of the current information content data 422 is extracted from the current user interaction data 440.

In one embodiment, once the relevant user interaction data has been extracted from the current user interaction data 440, the baseline user interaction data 434 is analyzed to determine the data in the baseline user interaction data 434 that corresponds to the relevant user interaction data. The current user interaction data 440 is then compared to the corresponding data in the baseline user interaction data 434 to determine whether there is any differential between the current user interaction data 440 and the corresponding data in the baseline user interaction data 434. Current user interaction data analysis module 442 then generates current user interaction differential data 444, which represents any such differential between the current user interaction data 440 and the corresponding data in the baseline user interaction data 434.

In one embodiment, once the current user interaction data 440 is analyzed along with the baseline user interaction data 434 to generate current user interaction differential data 444, differential comparator module 446 compares the current user interaction differential data 444 for one or more types of user interaction data with the threshold user interaction differential data 438 corresponding to the same one or more types of user interaction data to determine whether one or more of the current user interaction differentials in current user interaction differential data 444 is greater than the corresponding threshold user interaction differentials in threshold user interaction differential data 438.

For example, in one embodiment, the current user interaction differential associated with user interaction speed may be compared to the threshold interaction differential associated with user interaction speed, and the current user interaction differential associated with user comprehension level may be compared to the threshold interaction differential associated with user comprehension level. In this example, the comparison may yield that none, one, or both of the user interaction differentials is greater than their corresponding threshold interaction differentials.

In one embodiment, once the current user interaction differential data 444 is compared with the threshold user interaction differential data 438, if one or more of the current user interaction differentials is found, by differential comparator module 446, to be greater than the corresponding threshold interaction differentials, this may be identified as an anomaly in the psychological state of the user, and one or more actions may be taken, as determined by action determination module 448.

In one embodiment, the actions to be taken may be determined by action determination module 448 based on the severity of the anomaly. For example, if the anomaly is minor, then action determination module 448 may determine that actions should be taken to make slight adjustments to the information content data 422 and/or the user experience data 424 that is presented to the user through the user interface 420. On the other hand, if the anomaly is severe, then action determination module 448 may determine that actions should be taken to make major adjustments to the information content data 422 and/or the user experience data 424 that is presented to the current user through the user interface 420. In other embodiments, action determination module 448 may determine that more extreme actions should be taken. For example, if a user is determined to be in a severely anxious mental state, action determination module 448 may determine that actions such as emergency notifications and personal intervention are appropriate.

In various embodiments, once action determination module 448 determines actions to be taken, control proceeds to action execution module 450 for execution of the determined actions. Action execution may include, for example, selecting and providing different information content data 422 or user experience data 424 that is more appropriate for the current user's psychological state, contacting the user through any user approved contact means, and/or contacting a user's trusted third party on behalf of the user.

Figure 5:
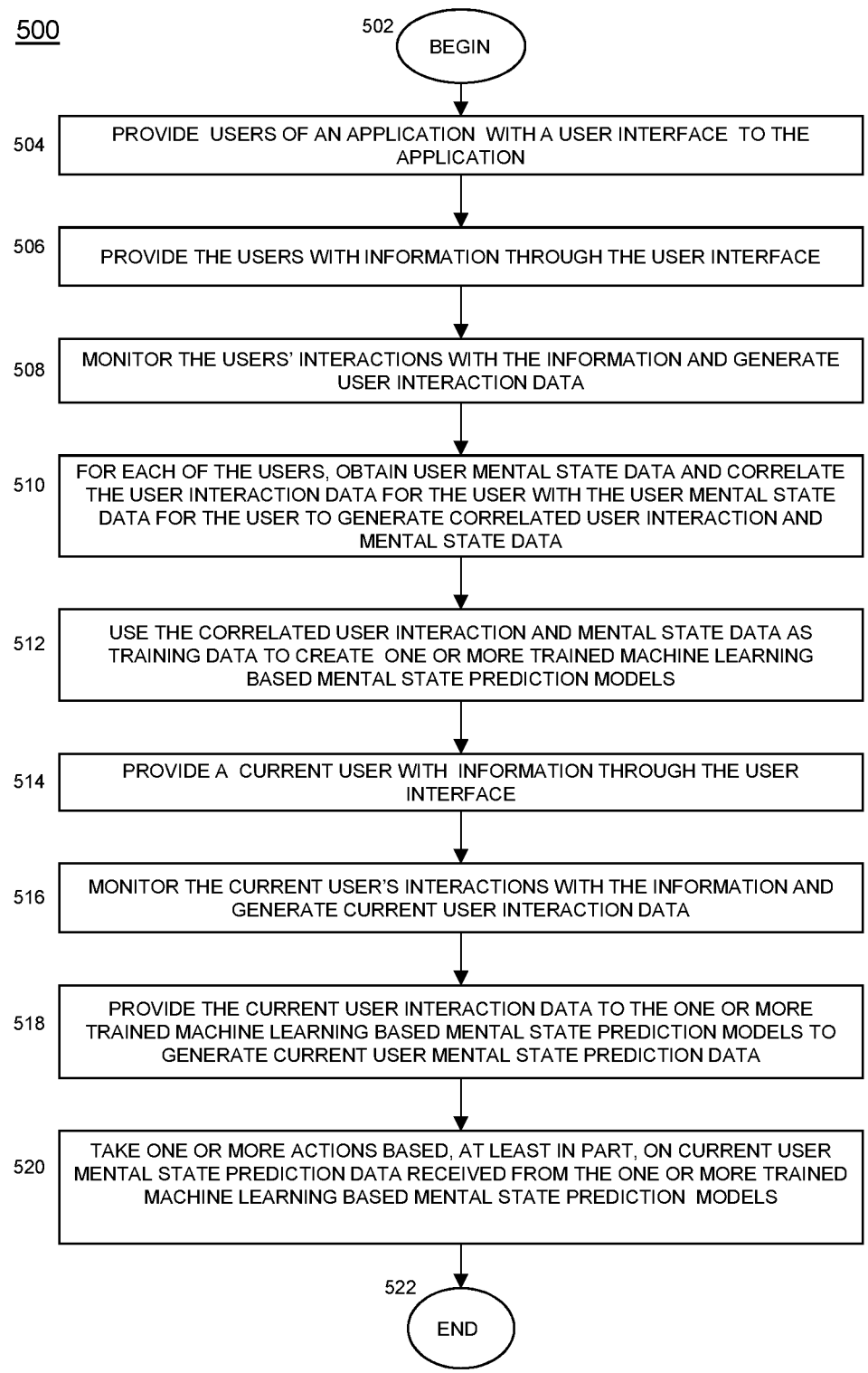
FIG. 5 is a flow chart of a process for remotely identifying or predicting the psychological state of application users based on machine learning-based analysis and processing in accordance with a third embodiment.

FIG. 5 is a flow chart of a process 500 for remotely identifying or predicting the psychological state of application users based on machine learning-based analysis and processing in accordance with a third embodiment.

Process 500 begins at BEGIN 502 and process flow proceeds to 504. At 504, one or more users of an application are provided with a user interface, which allows the one or more users to receive output from the application, as well as to provide input to the application.

In various embodiments, the application may be any type of application that is capable of providing content/information to a user through a user interface, including, but not limited to, a desktop computing system application, a mobile computing system application, a virtual reality computing system application, an application provided by an Internet of Things (IoT) device, or any combination thereof. In various embodiments, the user interface may include any combination of a graphical user interface, an audio-based user interface, a touch-based user interface, or any other type of user interface currently known to those of skill in the art, or any other type of user interface that may be developed after the time of filing.

In one embodiment, the application provided to the one or more users is a digital therapeutics application, which is designed to assist patients who have been diagnosed with one or more medical conditions. As a specific illustrative example, upon diagnosing a patient with one or more medical conditions, a medical care professional may prescribe the patient access to the digital therapeutics application. The digital therapeutics application may be accessed by the patient through any type of computing system that is capable of providing a user interface to a user, as discussed above. Upon accessing the digital therapeutics application, the patient then becomes a user of the application, and is provided with a user interface, which enables the user to interact with the digital therapeutics application.

In one embodiment, once one or more users of an application are provided with a user interface at 504, process flow proceeds to 506. At 506, the one or more users are provided with information through the user interface.

In various embodiments, the information provided to the one or more users through the user interface includes, but is not limited to, textual information, audio information, graphical information, image information, video information, and/or any combination thereof. In one embodiment, the information is provided to the one or more users in such a way that allows the one or more users to interact with the information provided. For example, a user may be presented with information on the screen of an electronic device, along with a variety of graphical user elements, which allow the user to scroll through the information, click on buttons associated with the information, and/or enter textual strings in response to the information. When the information is presented to a user on a device that includes a touch screen, the interaction may include touch-based interactions and/or gesture recognition. In addition to textual inputs and touch or click-based inputs, in various embodiments, the user may be able to interact with the information through more advanced input mechanisms such as through audio input, video input, accelerometer input, voice recognition, facial recognition or through a variety of physiological sensors. Examples of physiological sensors may include, but are not limited to, heart rate monitors, blood pressure monitors, eye tracking monitors, or muscle activity monitors.

As one specific illustrative example, in one embodiment, once one or more users of a digital therapeutics application are provided with a user interface, they may be provided with content-based information such as, but not limited to, information related to medical history, current or potential medical care providers, medical conditions, medications, nutritional supplements, advice or suggestions regarding diet and/or exercise, or any other type of information that may be considered relevant to the one or more users.

In one embodiment, the content-based information may be provided solely in a text format, however in various other embodiments, a user may also be presented with images that accompany the text, for example, images that depict one or more visual symptoms related to the user's medical conditions. The user may further be presented with graphical content, such charts, graphs, digital simulations, or other visualization tools. As one illustrative example, a user might be presented with a chart or graph that compares the user's symptoms with those of other patients diagnosed with the same or similar conditions. The user may further be presented with audio and/or video information related to their medical conditions. As additional illustrative examples, the user may be provided with one or more instructional videos that guide the user through physical therapy exercises, or educational videos that inform the user about the history and/or science behind their medical conditions. In various embodiments, the user may be presented with any combination of the above types of content-based information, or any other additional types of content that may be relevant to the particular user.

In addition to the types of content-based information discussed above, another type of information that may be provided to the one or more users is aesthetics-based information. This type of information may not be immediately recognized by a user, but it nevertheless plays an important role in the way in which the user absorbs and reacts to the presentation of the content-based information. This aesthetics-based information is used to create the overall user experience that is provided to a user by an application, and thus may also be referred to herein as user experience information, or user experience data. Examples of user experience data include, but are not limited to, the colors and fonts used to present the content-based information to a user, the various shapes of the graphical user interface elements, the layout or ordering of the content-based information presented to a user, and/or the sound effects, music, or other audio elements that may accompany the presentation of or interaction with the content-based information.

In one embodiment, once the one or more users are provided with information through the user interface at 506, process flow proceeds to 508. At 508, the interactions of the one or more users with the information presented through the user interface are monitored and user interaction data is generated.

The interactions of one or more users with the information presented through the user interface may be monitored through collection of user input data received through the user interface. The user input data collected may include, but is not limited to, data associated with click-stream input, textual input, touch input, gesture input, audio input, image input, video input, accelerometer input, and/or physiological input. In one embodiment, once the user input data is collected from the one or more users, the user input data from each of the one or more users is processed and aggregated to generate user interaction data.

As one illustrative example, in one embodiment, a digital therapeutics application may be configured to monitor specific types of user interaction data, in order to enable further data analysis and processing. In one embodiment, the digital therapeutics application may be configured to monitor the speed at which one or more users interact with the information provided. In one embodiment, the speed at which a user interacts with the information provided may be measured by collecting clickstream data, which may include data such as how long a user spends engaging with various parts of the information content presented to the user.

For example, consider the situation where a user of a digital therapeutics application is presented with a lengthy article related to one or more of their medical conditions. In this example, the user would likely need to fully scroll through the content to read the entire article. The time it takes for a user to scroll from the top of the text to the bottom of the text may be determined from the user input data, and this input data could then be used to generate user interaction data representing the speed at which the user read, or interacted, with the article.

As a further example, a user of a digital therapeutics application may be presented with a series of screens, where each screen may contain one or more types of information related to the user's medical conditions. For instance, the first screen may include text and images, the second screen may include one or more graphical visualizations, and the third screen may include an audio/video presentation, along with textual information. Each screen may have user interface elements, such as navigation buttons, allowing the user to move forward and backwards between the different screens. The time it takes the user to click or touch from one screen to the next, or from the beginning to the end of the presentation may be determined from the user input data, and this input data could then also be used to generate user interaction data representing the speed at which the user read, or interacted with, the presentation.

Additionally, a user may be presented with a variety of questions or exercises requiring textual responses, and the frequency of the typing and deleting events could be used to generate user interaction data representing the speed at which the user interacted with the exercise materials.

In another embodiment, the digital therapeutics application may be configured to monitor one or more users' interactions with the information to determine the one or more users' level of comprehension with respect to that information. In one embodiment, the level of comprehension associated with a user and the information provided to the user may be measured by periodically presenting the user with a variety of prompts or questions designed to determine whether the user is engaged with and understanding the information being presented. A comprehension level may then be calculated, for example, based on the percentage of questions that the user answered correctly.

Further, in one embodiment, a user's level of comprehension may be determined based on the percentage of the provided information that the user read or interacted with. For example, if a user begins reading an article, but the user input data indicates that the user never scrolls to the end of the article, it may be determined that the user has poor comprehension of the information provided. Likewise, in the case where a user is presented with multiple screens of information, for example, ten screens, if the user only navigates to two of the ten screens, then it may be determined that the user has poor comprehension of the information provided.

It should be noted here, that the foregoing examples are given for illustrative purposes only, and are not intended to limit the scope of the invention as disclosed herein and as claimed below.

In one embodiment, once the interactions of the one or more users with the information presented through the user interface are monitored and the associated user interaction data is generated at 508, process flow proceeds to 510. In one embodiment, at 510, user mental state data is obtained for each of the one or more users, and the user interaction data for each of the one or more users is correlated with the mental state data corresponding to each of the one or more users.

In one embodiment, at 510 the user mental state data is obtained from the one or more users by interviewing each of the one or more users before, after, or during generation of the user interaction data at 508. In some embodiments, at 510, the user mental state data is obtained by consulting with a third party, such as a medical professional associated with the user, before or after the user interaction data is generated at 508. In some embodiments, at 510 the user mental state data is obtained from data in one or more files associated with a user indicating none or more events occurring before or after the user interaction data is generated at 508. Such events may include, but are not limited to, a change in diagnosis of the user's health, a change in medication, or any other event indicating the mental state of the user at or near the time the user interaction data was generated at 508.

Once user mental state data is obtained for one or more users, indicating the mental state of each user at or near the time the user interaction data was generated, the user mental state data for each user is correlated with the user interaction data that was generated for that user at 508. The correlated user mental state data and user interaction data for each of the one or more users is then aggregated to generate correlated user interaction and mental state data.

In one embodiment, once the correlated user interaction and mental state data is generated at 510, process flow proceeds to 512. In one embodiment, at 512, the correlated user interaction and mental state data is used as training data to create one or more trained machine learning based mental state prediction models.

In various embodiments, and largely depending on the machine learning based models used, the user interaction and/or mental state data is processed using various methods know in the machine learning arts to identify elements and vectorize the user interaction and/or mental state data. As a specific illustrative example, in a case where the machine leaning based model is a supervised model, the user interaction data can be analyzed and processed to identify individual elements found to be indicative of a user's mental state. These individual elements are then used to create user interaction data vectors in multidimensional space which are, in turn, used as input data for training one or more machine learning models. The mental state data for a user that correlates with the user interaction data vector associated with that user is then used as a label for the resulting vector. In various embodiments, this process is repeated for the user interaction and mental state data received from each of the one or more users, such that multiple, often millions, of correlated pairs of user interaction data vectors and mental state data are used to train one or more machine learning based models. Consequently, this process results in the creation of one or more trained machine learning based mental state prediction models.

Those of skill in the art will readily recognize that there are many different types of machine learning based models known in the art, and as such, it should be noted that the specific illustrative example of a supervised machine learning based model discussed above should not be construed as limiting the embodiments set forth herein.

For instance, in various embodiments, the one or more machine learning based models can be one or more of supervised machine learning-based models; semi supervised machine learning-based models; unsupervised machine learning-based models; classification machine learning-based models; logistical regression machine learning-based models; neural network machine learning-based models; deep learning machine learning-based models; and/or any other machine learning based models discussed herein, known at the time of filing, or as developed/made available after the time of filing.

In one embodiment, once the correlated user interaction and mental state data is used as training data to create one or more trained machine learning based mental state prediction models at 512, process flow proceeds to 514. In one embodiment, at 514, a current user of the application is provided with information through the user interface of the application.

In contrast to operation 506 described above, where one or more users are provided with information through the application user interface, at 514, a single specific user is provided with information through the user interface of the application, during a single current session of using the application. Therefore, the single specific user may hereafter be referred to as the current user.

As described in detail above, with respect to information provided to one or more users, in various embodiments, the information provided to the current user through the user interface includes, but is not limited to, textual information, audio information, graphical information, image information, video information, user experience information, and/or any combination thereof. In one embodiment, the information is provided to the current user in such a way that allows the current user to interact with the information provided.

In one embodiment, once information is provided to a current user at 514, process flow proceeds to 516. In contrast to operation 508 described above, where one or more users' interactions with the information provided through the user interface are monitored to generate user interaction data, at 516, the current user's interactions with the information provided through the user interface are monitored to generate current user interaction data.

As described in detail above, with respect to monitoring the interactions of one or more users to generate user interaction data, in various embodiments, the interactions of the current user with the information presented through the user interface may be monitored through collection of user input data received through the user interface. The user input data collected may include, but is not limited to, data associated with click-stream input, textual input, touch input, gesture input, audio input, image input, video input, accelerometer input, and/or physiological input. In one embodiment, once the user input data is collected from the current user, the user input data is processed and aggregated to generate current user interaction data.

As also described in detail above, with respect to monitoring the interactions of one or more users to generate collective user interaction data, in various embodiments, the application may be configured to monitor specific types of current user interaction data, such as, but not limited to, the speed at which the current user interacts with the information provided, and/or the current user's level of comprehension with respect to the information provided. In one embodiment, the speed at which the current user interacts with the information provided may be measured by collecting clickstream data, which may include data such as how long the current user spends engaging with various parts of the information content presented to the current user through the user interface. In one embodiment, the level of comprehension associated with the current user and the information provided may be measured by periodically presenting the current user with a variety of prompts or questions designed to determine whether the current user is engaged with and understanding the information being presented. A comprehension level may then be calculated, for example, based on the percentage of questions that the current user answered correctly. Further, in one embodiment, the current user's level of comprehension may be determined based on the percentage of the provided information that the current user read or interacted with.

In one embodiment, once the current user's interactions with the information provided through the user interface are monitored to generate current user interaction data at 516, process flow proceeds to 518. In one embodiment, at 518, the current user interaction data is provided to the one or more trained machine learning based mental state prediction models to generate current user mental state prediction data.

In one embodiment, the current user interaction data generated at 516 is vectorized to generate one or more user interaction data vectors. The one or more user interaction data vectors associated with the current user are then provided as input data to the one or more trained machine learning based mental state prediction models. The current user interaction vector data is then processed to find a distance between the one or more current user interaction data vectors and one or more previously labeled user interaction data vectors, where the previously labeled user interaction data vectors are vectors with known associated user mental state data. In one embodiment, one or more probability scores are determined based on a calculated distance between the current user interaction vector data and the previously labeled user interaction vector data. Upon determination that the one or more current user interaction data vectors correlate to a user mental state associated with the previously labeled user interaction vector data, current user mental state prediction data is generated. In one embodiment, the current user mental state prediction data comprises one or more probability scores, which indicate the probability that the current user is in one or more particular mental states.

In one embodiment, once current user mental state prediction data is generated at 518, process flow proceeds to 520. At 520, one or more actions are taken based, at least in part, on current user mental state prediction data received from the one or more trained machine learning based mental state prediction models.

In one embodiment, the one or more actions to be taken may be determined based on the current user mental state prediction data. For example, if the current user mental state prediction data indicates that the current user is mildly anxious, then actions might be taken to make slight adjustments to the information content data and/or the user experience data that is presented to the current user. On the other hand, if the current user mental state prediction data indicates that the current user is severely anxious, then actions might be taken to make major adjustments to the information content data and/or the user experience data that is presented to the current user. In one embodiment, adjustments to the information content data may include adjustments such as, but not limited to, providing textual content that uses gentler language, providing audio content that includes quieter, more relaxing voices, sounds, or music, or providing image/video content that is less realistic or less graphic. Adjustments to the user experience data may include adjustments such as, but not limited to, changing the colors, fonts, shapes, presentation, and/or layout of the information content data presented to the current user.

For example, in one embodiment, as discussed above, the application is a digital therapeutics application, and the current user is a patient who has been diagnosed with a medical condition. Many patients experience a great deal of anxiety related to their medical conditions. If the predictive mental state data indicates that a user may be suffering from anxiety, or may otherwise be in psychological distress, a decision may be made that the current user would benefit from assistance, or from adjustments designed to reduce the current user's anxiety level.

As one specific illustrative example, if a determination is made that the current user is mildly anxious, minor actions may be taken to reduce the current user's anxiety level, such as adjusting the content and/or presentation of the information that is being provided to the current user through the user interface. As one simplified illustrative example, cool colors such as blue and violet are known to produce calming effects, and rounder, softer shapes are also associated with calming effects. So in this situation, the user experience content data may be modified so that the content is presented to the user with a blue/violet color scheme, and the graphical user elements may be changed to include rounder and softer shapes. As another specific illustrative example, if a determination is made that the current user is extremely anxious, then more extreme actions may be taken, such as notifying one or more medical professionals associated with the user through a notification system of the application, or some other form of personal intervention from one or more medical professionals associated with the current user.

In various embodiments several additional types of actions may be appropriate specifically when dealing with users who have been diagnosed with one or more medical conditions, such as, but not limited to: asking the user for input and/or response data; alerting the user; alerting one or more of the user's mental health or medical professionals; making notes in, adding data to, or highlighting the user's electronic file; making a specialist referral; recommending support contacts to the user; prescribing additional appointments, treatments, actions, or medications; calling emergency response or intervention professionals; notifying emergency contacts, relatives, or caregivers, etc.

In one embodiment, once one or more actions are taken based, at least in part, on current user mental state prediction data at 520, process flow proceeds to END 522 and the process 500 for remotely identifying or predicting the psychological state of application users based on machine learning-based analysis and processing is exited to await new data and/or instructions.

Figure 6:
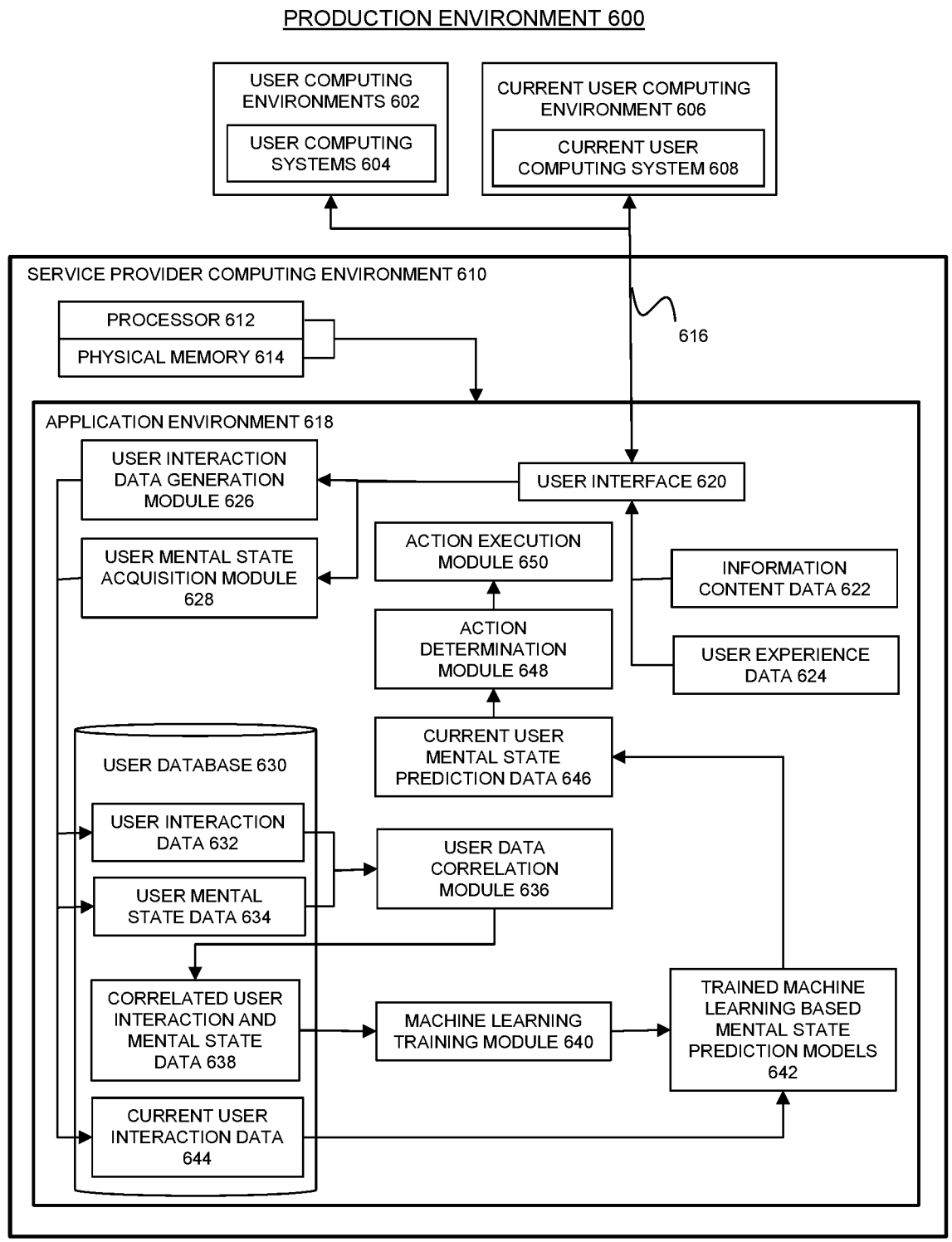
FIG. 6 is a block diagram of a production environment for remotely identifying or predicting the psychological state of application users based on machine learning-based analysis and processing in accordance with a third embodiment.

FIG. 6 is a block diagram of a production environment 600 for remotely identifying or predicting the psychological state of application users based on machine learning-based analysis and processing in accordance with a third embodiment.

In one embodiment, production environment 600 includes user computing environments 602, current user computing environment 606, and service provider computing environment 610. User computing environments 602 and current user computing environment 606 further comprise user computing systems 604 and current user computing system 608, respectively. The computing environments 602, 606, and 610 are communicatively coupled to each other with one or more communication networks 616.

In one embodiment, service provider computing environment 610 includes processor 612, physical memory 614, and application environment 618. Processor 612 and physical memory 614 coordinate the operation and interaction of the data and data processing modules associated with application environment 618. In one embodiment, application environment 618 includes user interface 620, which is provided to user computing systems 604 and current user computing system 608 through the one or more communication networks 616.

In one embodiment, application environment 618 further includes user interaction data generation module 626, user mental state acquisition module 628, user data correlation module 636, machine learning training module 640, action determination module 648, and action execution module 650, each of which will be discussed in further detail below.

Additionally, in one embodiment, application environment 618 includes information content data 622, user experience data 624, user interaction data 632, user mental state data 634, correlated user interaction and mental state data 638, current user interaction data 644, trained machine learning based mental state prediction models 642, and current user mental state prediction data 646, each of which will be discussed in further detail below. In some embodiments, user interaction data 632, user mental state data 634, correlated user interaction and mental state data 638, and current user interaction data 644 may be stored in user database 630, which includes data associated with one or more users of application environment 618.

In one embodiment, user computing systems 604 of user computing environments 602, which are associated with one or more users of application environment 618, are provided with a user interface 620, which allows the one or more users to receive output from the application environment 618, as well as to provide input to the application environment 618, through the one or more communication networks 616.

As discussed above, in various embodiments, the application environment 618 may be any type of application environment that is capable of providing a user interface and content/information to a user, including, but not limited to, a desktop computing system application, a mobile computing system application, a virtual reality computing system application, an application provided by an Internet of Things (IoT) device, or any combination thereof. Further, in various embodiments, the user interface 620 may include any combination of a graphical user interface, an audio-based user interface, a touch-based user interface, or any other type of user interface currently known to those of skill in the art, or any other type of user interface that may be developed after the time of filing.

In one embodiment, user computing systems 604 of user computing environments 602, which are associated with one or more users of application environment 618, are provided with information content data 622 and user experience data 624 through the user interface 620.

In various embodiments, the information content data 622 provided to the one or more users through the user interface 620 includes, but is not limited to, textual information, audio information, graphical information, image information, video information, and/or any combination thereof. In one embodiment, the information content data 622 is provided to the one or more users in such a way that allows the one or more users to interact with the information content data 622.

In various embodiments, the user experience data 624 includes, but is not limited to, colors and fonts used to present the information content data 622 to a user, the various shapes of graphical user interface elements, the layout or ordering of the information content data 622, and/or the sound effects, music, or other audio elements that may accompany the presentation of or interaction with the information content data 622.

In one embodiment, once the one or more users are provided with information content data 622 and user experience data 624 through the user interface 620, the interactions of the one or more users with the information content data 622 are monitored by user interaction data generation module 626 through collection of user input data received through the user interface 620. The user input data collected by user interaction data generation module 626 may include, but is not limited to, data associated with click-stream input, textual input, touch input, gesture input, audio input, image input, video input, accelerometer input, and/or physiological input. In one embodiment, once the user input data is collected by user interaction data generation module 626, the user input data from each of the one or more users is processed and aggregated by user interaction data generation module 626 to generate user interaction data 632.

In various embodiments, user interaction data may include data such as, but not limited to, the number of times a user accesses the application environment 618, the length of time a user spends engaging with the application environment 618, how long a user has had access to the application environment 618, the type of information content data 622 that a user engages with the most while using the application environment 618, whether or not a user utilizes advanced input mechanisms that may be provided by user interface 620, the type of input mechanisms most preferred by a user, the speed at which a user interacts with the information content data 622 presented through the user interface 620, and the level of comprehension a user has of the information content data 622 presented through the user interface 620.

In one embodiment, once user interaction data 632 has been generated by user interaction data generation module 626, user mental state data 634 is obtained for each of the one or more users by user mental state acquisition module 628, and the user interaction data 632 for each of the one or more users is correlated with the user mental state data 634 corresponding to each of the one or more users. In one embodiment the user mental state data 634 is obtained from the one or more users by user mental state acquisition module 628, before, after, or during generation of the user interaction data 632 by user interaction data generation module 626. In various embodiments, the user mental state acquisition module 628 acquires the user mental state data 634 through various mechanisms, such as, but not limited to, interviewing the user, consulting with a third party, such as a medical professional associated with the user, and/or obtaining and analyzing one or more files associated with a user.

Once user mental state data 634 is obtained for one or more users by user mental state acquisition module 628, the user mental state data 634 for each user is correlated with the associated user interaction data 632 by user data correlation module 636. The correlated user mental state data 634 and user interaction data 632 for each of the one or more users is then aggregated by user data correlation module 636 to generate correlated user interaction and mental state data 638.

In one embodiment, once the correlated user interaction and mental state data 638 is generated by user data correlation module 636, the correlated user interaction and mental state data 638 is used as training data by machine learning training module 640 to create one or more trained machine learning based mental state prediction models 642.

In various embodiments, and largely depending on the machine learning based models used, the correlated user interaction and mental state data 638 is processed by machine learning training module 640, using various methods know in the machine learning arts to identify elements and vectorize the correlated user interaction and mental state data 638. As a specific illustrative example, in a case where the machine leaning based model is a supervised model, the user interaction data 632 can be analyzed and processed to identify individual elements found to be indicative of a user's mental state. These individual elements are then used to create user interaction data vectors in multidimensional space which are, in turn, used as input data for training one or more machine learning models. The user mental state data 634 that correlates with the user interaction data vector associated with that user is then used as a label for the resulting vector. In various embodiments, this process is repeated by machine learning training module 640 for the user interaction data 632 and user mental state data 634 received from each of the one or more users, such that multiple, often millions, of correlated pairs of user interaction data vectors and mental state data are used to train one or more machine learning based models. Consequently, this process results in the creation of one or more trained machine learning based mental state prediction models 642.

In one embodiment, once the correlated user interaction and mental state data 638 is used as training data by machine learning training module 640 to create one or more trained machine learning based mental state prediction models 642, current user computing system 608 of user computing environment 606, which is associated with a current user of application environment 618, is provided with information content data 622 and user experience data 624 through the user interface 620.

In one embodiment, once the current user is provided with information content data 622 and user experience data 624 through the user interface 620, the interactions of the current user with the information content data 622 are monitored by user interaction data generation module 626 through collection of user input data received through the user interface 620. The user input data collected by user interaction data generation module 626 may include, but is not limited to, data associated with click-stream input, textual input, touch input, gesture input, audio input, image input, video input, accelerometer input, and/or physiological input. In one embodiment, once the current user input data is collected by user interaction data generation module 626, the current user input data is processed and aggregated by user interaction data generation module 626 to generate current user interaction data 644.

In one embodiment, once current user interaction data 644 has been generated by user interaction data generation module 626, the current user interaction data 644 is provided to the one or more trained machine learning based mental state prediction models 642 to generate current user mental state prediction data 646.

In one embodiment, the current user interaction data 644 is vectorized to generate one or more user interaction data vectors. The one or more user interaction data vectors associated with the current user are then provided as input data to the one or more trained machine learning based mental state prediction models 642, resulting in the generation of current user mental state prediction data 646. In one embodiment, the current user mental state prediction data 646 comprises one or more probability scores, which indicate the probability that the current user is in one or more particular mental states.

In one embodiment, once current user mental state prediction data 646 is generated by the one or more trained machine learning based mental state prediction models 642, one or more actions are taken based, at least in part, on the current user mental state prediction data 646.

In one embodiment, the one or more actions to be taken may be determined by action determination module 648 based on the current user mental state prediction data 646. For example, if current user mental state prediction data 646 indicates that the current user is mildly anxious, then action determination module 648 may determine that actions should be taken to make slight adjustments to the information content data 622 and/or the user experience data 624 that is presented to the current user through the user interface 620. On the other hand, if the current user mental state prediction data 646 indicates that the current user is severely anxious, then action determination module 648 may determine that actions should be taken to make major adjustments to the information content data 622 and/or the user experience data 624 that is presented to the current user through the user interface 620. In other embodiments, action determination module 648 may determine that more extreme actions should be taken. For example, if the current user mental state prediction data 646 indicates that the current user is severely anxious, then action determination module 648 may determine that actions such as emergency notifications and personal intervention are appropriate.

In various embodiments, once action determination module 648 determines actions to be taken, control proceeds to action execution module 650 for execution of the determined actions. Action execution may include, for example, selecting and providing different information content data 622 or user experience data 624 that is more appropriate for the current user's psychological state, contacting the user through any user approved contact means, and/or contacting a user's trusted third party on behalf of the user.

The embodiments disclosed above provide an effective and efficient technical solution to the technical problem of remotely identifying and monitoring changes or anomalies in the psychological state of application users. One specific practical application of the disclosed embodiments is that of remotely identifying and monitoring changes or anomalies in the psychological state of patients who have been diagnosed with one or more medical conditions. In the disclosed embodiments, a patient diagnosed with one or more medical conditions is prescribed access to a digital therapeutics application, which is designed to provide guided care to the patient in a variety of ways. Through the digital therapeutics application, the patient may be provided with information, such as information relating to one or more of the patient's medical conditions, as well as current and potential medications and/or treatments. In addition, the digital therapeutics application disclosed herein further provides the patient with interactive content, which allows for the collection of data related to aspects of the patient's interaction with the provided content. The collected interaction data is then analyzed to identify and monitor changes or anomalies in the psychological state of the patient. Upon identification of changes or anomalies in the patient's psychological state, one or more actions are taken to assist the patient.

Consequently, the embodiments disclosed herein are not an abstract idea, and are well-suited to a wide variety of practical applications. Further, many of the embodiments disclosed herein require processing and analysis of billions of data points and combinations of data points, and thus, the technical solution disclosed herein cannot be implemented solely by mental steps or pen and paper, is not an abstract idea, and is, in fact, directed to providing technical solutions to long-standing technical problems associated with remotely monitoring the psychological state of application users.

Additionally, the disclosed method and system for remotely monitoring the psychological state of application users requires a specific process comprising the aggregation and detailed analysis of large quantities of user input and interaction data, and as such, does not encompass, embody, or preclude other forms of innovation in the area of psychological monitoring. Further, the disclosed embodiments of systems and methods for remotely monitoring the psychological state of application users are not abstract ideas for at least several reasons.

First, effectively and efficiently monitoring the psychological state of application users remotely is not an abstract idea because it is not merely an idea in and of itself. For example, the process cannot be performed mentally or using pen and paper, as it is not possible for the human mind to identify, process, and analyze all possible combinations of user inputs, user interactions, and user psychological states, even with pen and paper to assist the human mind and even with unlimited time.

Second, effectively and efficiently monitoring the psychological state of application users remotely is not a fundamental economic practice (e.g., is not merely creating a contractual relationship, hedging, mitigating a settlement risk, etc.).

Third, effectively and efficiently monitoring the psychological state of application users remotely is not merely a method of organizing human activity (e.g., managing a game of bingo). Rather, in the disclosed embodiments, the method and system for effectively and efficiently monitoring the psychological state of application users remotely provides a tool that significantly improves the fields of medical and mental health care. Through the disclosed embodiments, patients are provided with unique and personalized remote assistance, treatment, and care. As such, the method and system disclosed herein is not an abstract idea, and also serves to integrate the ideas disclosed herein into practical applications of those ideas.

Fourth, although mathematics may be used to implement the embodiments disclosed herein, the systems and methods disclosed and claimed herein are not abstract ideas because the disclosed systems and methods are not simply a mathematical relationship/formula.

It should be noted that the language used in the specification has been principally selected for readability, clarity, and instructional purposes, and may not have been selected to delineate or circumscribe the inventive subject matter. Accordingly, the disclosure of the present invention is intended to be illustrative, but not limiting, of the scope of the invention, which is set forth in the claims below.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, or protocols. Further, the system or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic or algorithm-like descriptions and representations are the means used by those of skill in the art to most effectively and efficiently convey the substance of their work to others of skill in the art. These operations, while described functionally or logically, are understood to be implemented by computer programs or computing systems. Furthermore, it has also proven convenient at times to refer to these arrangements of operations as steps or modules or by functional names, without loss of generality.

In addition, the operations shown in the figures, or as discussed herein, are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A computing system implemented method comprising:
   identifying one or more physiological conditions of one or more users;
   providing a digital therapeutic system to the one or more users;
   providing, by one or more processors of the digital therapeutic system, the one or more users of the therapeutic application with therapeutic content through a user interface of the digital therapeutic system, wherein the therapeutic content provides treatment for one or more of the physiological conditions of the one or more patient users;
   remotely monitoring, by one or more processors of the digital therapeutic system, interactions of the one or more patient users with the therapeutic content provided through the user interface to generate user interaction data representing the interactions of the one or more users with the therapeutic content during a defined period of time;
   for each of the one or more users, obtaining mental state data for the user during the defined period of time in which the user is interacting with the therapeutic content;
   for each of the one or more users, correlating each user's user interaction data with that user's mental state data;
   collecting and processing the correlated user interaction data and user mental state data for each of the one or more users to generate machine learning-based mental state prediction model training data;
   providing the machine learning-based mental state prediction model training data to one or more machine learning-based prediction models to generate one or more trained machine learning-based mental state prediction models;
   identifying one or more physiological conditions of a current patient user;
   providing the digital therapeutic system to the current patient user;
   digitally generating, by one or more processors of the digital therapeutic system, current therapeutic content, wherein the current therapeutic content provides the current patient user with treatment for one or more of the current patient user's physiological conditions;
   providing, by one or more processors of the digital therapeutic system, the current patient user with the digitally generated current therapeutic content through the user interface of the digital therapeutic system during a current session of the current patient user interacting with the digital therapeutic system;
   remotely monitoring, by one or more processors of the digital therapeutic system, interactions of the current patient user with the therapeutic content provided through the user interface to generate current patient user interaction data representing the interactions of the current patient user with the therapeutic content during the current session;
   providing the current patient user interaction data to the one or more trained machine learning-based mental state prediction models;
   receiving current patient user mental state prediction data from the one or more trained machine learning-based mental state prediction models; and
   based, at least in part, on the current patient user mental state prediction data received from the one or more trained machine learning-based mental state prediction models;
   digitally generating, by one or more processors of the digital therapeutic system, during the current session, dynamically modified current therapeutic content based at least in part on the current patient user mental state prediction data; and automatically providing, using one or more processors of the digital therapeutic system, during the current session, the current patient user with the dynamically modified current therapeutic content through a graphical user interface of the digital therapeutic system.

2. The computing system implemented method of claim 1 wherein the therapeutic content provided through the user interface of the digital therapeutic system includes one or more of:
textual information related to the current patient user's one or more physiological conditions;
audio information related to the current patient user's one or more physiological conditions;
graphical information related to the current patient user's one or more physiological conditions;
image information related to the current patient user's one or more physiological conditions; and
video information related to the current patient user's one or more physiological conditions.

3. The computing system implemented method of claim 1 wherein monitoring the interactions of the one or more users and the current patient user includes monitoring the speed at which a user interacts with the therapeutic content provided through the user interface.

4. The computing system implemented method of claim 3 wherein the speed at which a user interacts with the therapeutic content provided through the user interface is measured by monitoring one or more of:
the speed at which a user scrolls through the therapeutic content provided through the user interface;
the speed at which a user clicks through the therapeutic content provided through the user interface; and
the speed at which a user enters text through the user interface.

5. The computing system implemented method of claim 1 wherein monitoring the interactions of the one or more users or the current patient user includes monitoring a user's comprehension of the therapeutic content provided through the user interface.

6. The computing system implemented method of claim 5 wherein a user's comprehension of the therapeutic content provided through the user interface is measured by one or more of:
presenting the user with questions related to the provided therapeutic content; and
determining a percentage of the provided therapeutic content that the user has interacted with.

7. The computing system implemented method of claim 1 wherein, upon receiving the current patient user mental state prediction data, one or more actions are taken, including one or more of:
adjusting presentation of the therapeutic content provided to the patient user;
adjusting the therapeutic content provided to the patient user;
requesting information from the patient user;
contacting the patient user directly;
contacting a third party on the patient user's behalf;
adding a note to the patient user's file for review by a third party; and
flagging the patient user's file for attention by a third party.

8. The computing system implemented method of claim 7 wherein the third party is one or more of:
a medical professional associated with the patient user;
an emergency contact associated with the patient user; and
a relative of the patient user.

9. The computing system implemented method of claim 1 wherein the one or more machine learning-based prediction models are of a type selected from the group of machine learning-based models including:
supervised machine learning-based models;
semi supervised machine learning-based models;
unsupervised machine learning-based models;
classification machine learning-based models;
logistical regression machine learning-based models;
neural network machine learning-based models; and
deep learning machine learning-based models.

10. A computing system implemented method comprising:
obtaining correlated user interaction and mental state data associated with one or more users of a digital therapeutic system;
processing the correlated user interaction and mental state data to generate machine learning-based mental state prediction model training data;
providing the machine learning-based mental state prediction model training data to one or more machine learning-based prediction models to generate one or more trained machine learning-based mental state prediction models;
identifying one or more physiological conditions of a current patient user;
providing the digital therapeutic system to the current patient user;
digitally generating, by one or more processors of the digital therapeutic system, current therapeutic content, wherein the current therapeutic content provides the current patient user with treatment for one or more of the current patient user's physiological conditions;
providing, by one or more processors of the digital therapeutic system, the current patient user with the digitally generated current therapeutic content through the user interface of the digital therapeutic system during a current session of the current patient user interacting with the digital therapeutic system;
remotely monitoring, by one or more processors of the digital therapeutic system, interactions of the current patient user with the therapeutic content provided through the user interface to generate current patient user interaction data representing the interactions of the current user with the therapeutic content during the current session;
providing the current patient user interaction data to the one or more trained machine learning-based mental state prediction models;
receiving current patient user mental state prediction data from the one or more trained machine learning-based mental state prediction models; and
based, at least in part, on the current patient user mental state prediction data received from the one or more trained machine learning-based mental state prediction models;
digitally generating, by one or more processors of the digital therapeutic system, during the current session, dynamically modified current therapeutic content based at least in part on the current patient user mental state prediction data; and
automatically providing, using one or more processors of the digital therapeutic system, during the current session, the current patient user with the dynamically modified current therapeutic content through a graphical user interface of the digital therapeutic system.

* * * * *